US011825837B2

(12) United States Patent
Nyambo et al.

(10) Patent No.: US 11,825,837 B2
(45) Date of Patent: Nov. 28, 2023

(54) DISPENSER AND METHOD OF USE THEREOF

(71) Applicant: S. C. Johnson & Son, Inc., Racine, WI (US)

(72) Inventors: Calistor Nyambo, Mt Pleasant, WI (US); Curtis Conklin, Racine, WI (US); Caitlin Y. O'Gara, Milwaukee, WI (US); Jia Wang, Racine, WI (US); Todd Ulrich, Racine, WI (US)

(73) Assignee: S. C. JOHNSON & SON, INC., Racine, WI (US)

( * ) Notice: Subject to any disclaimer, the term of this patent is extended or adjusted under 35 U.S.C. 154(b) by 21 days.

(21) Appl. No.: 16/431,598

(22) Filed: Jun. 4, 2019

(65) Prior Publication Data

US 2020/0383324 A1 Dec. 10, 2020

(51) Int. Cl.
*A01N 25/34* (2006.01)
*B29C 48/08* (2019.01)
*B29C 48/21* (2019.01)
*B29C 48/00* (2019.01)
*A01N 53/00* (2006.01)
*B32B 27/08* (2006.01)
*B32B 27/18* (2006.01)
*B32B 27/30* (2006.01)
*B32B 27/32* (2006.01)
*B32B 27/34* (2006.01)
*B29K 23/00* (2006.01)
*B29K 77/00* (2006.01)
*B29K 105/00* (2006.01)

(52) U.S. Cl.
CPC ............ *A01N 25/34* (2013.01); *A01N 53/00* (2013.01); *B29C 48/0021* (2019.02); *B29C 48/08* (2019.02); *B29C 48/21* (2019.02); *B32B 27/08* (2013.01); *B32B 27/18* (2013.01); *B32B 27/306* (2013.01); *B32B 27/32* (2013.01); *B32B 27/34* (2013.01); *B29K 2023/065* (2013.01); *B29K 2023/083* (2013.01); *B29K 2077/00* (2013.01); *B29K 2105/0011* (2013.01); *B32B 2250/05* (2013.01); *B32B 2250/24* (2013.01)

(58) Field of Classification Search
CPC .... A01N 25/34; A01N 53/00; B29C 48/0021; B29C 48/08; B29C 48/21; B32B 27/08; B32B 27/18; B32B 27/306; B32B 27/32; B32B 27/34; B32B 2250/05; B32B 2250/24; B29K 2023/065; B29K 2023/083; B29K 2077/00; B29K 2105/0011

See application file for complete search history.

(56) References Cited

U.S. PATENT DOCUMENTS

| | | |
|---|---|---|
| 4,145,001 A | 3/1979 | Weyenberg et al. |
| 4,661,388 A | 4/1987 | Charbonneau |
| 4,841,669 A | 6/1989 | Demarest et al. |
| 4,880,690 A | 11/1989 | Szycher et al. |
| 5,455,043 A | 10/1995 | Fischel-Ghodsian |
| 5,556,030 A | 9/1996 | Paul |
| 5,637,401 A | 6/1997 | Berman et al. |
| 5,656,282 A | 8/1997 | Cook et al. |
| 5,804,264 A | 9/1998 | Bowen |
| 6,079,146 A | 6/2000 | Larsen |
| 6,100,208 A | 8/2000 | Brown et al. |
| 6,244,265 B1 | 6/2001 | Cronk et al. |
| 6,260,477 B1 | 7/2001 | Tuyls et al. |
| 6,534,079 B1 | 3/2003 | Munagavalasa |
| 6,554,887 B1 | 4/2003 | Inglis |
| 6,582,714 B1 | 6/2003 | Emmrich et al. |
| 6,723,671 B2 | 4/2004 | Zolotarsky et al. |
| 6,902,817 B2 | 6/2005 | Bowen et al. |
| 6,938,832 B2 | 9/2005 | Sada |
| 7,600,668 B2 | 10/2009 | Pham |
| 3,142,804 A1 | 3/2012 | Barazani |
| 8,277,940 B2 | 10/2012 | Desiderio et al. |
| 8,298,520 B2 | 10/2012 | Itoi et al. |
| 8,931,711 B2 | 1/2015 | Gruenbacher et al. |
| 8,968,647 B2 | 3/2015 | Fischer et al. |
| 9,327,044 B2 | 5/2016 | Olchovy et al. |
| 9,675,723 B2 | 6/2017 | Chew |

(Continued)

FOREIGN PATENT DOCUMENTS

| | | | | |
|---|---|---|---|---|
| EP | 1082970 A1 | * | 3/2001 | ............... A61L 9/12 |
| WO | 8910146 A1 | | 11/1989 | |

(Continued)

OTHER PUBLICATIONS

International Search Report and Written Opinion of the International Searching Authority from corresponding Int'l Application No. PCT/US2020/035514, dated Oct. 15, 2020, (10 pages).

*Primary Examiner* — Robert S Cabral

(74) *Attorney, Agent, or Firm* — Quarles & Brady LLP

(57) ABSTRACT

A multi-layer article including a first non-active state and a second active state, the multi-layer article comprising an outer layer having a first side and a second side, an inner layer adjacent to at least a portion of the outer layer and including a volatile material, and an upper layer including a first side and a second side, the first side of the upper layer being adjacent to at least a portion of the inner layer. The multi-layer article is folded upon itself in the first non-active state so that at least a first portion of the second side of the upper layer is disposed on a top of a second portion of the second side of the upper layer, and the first portion and the second portion of the upper layer are heat sealed in the non-active state.

21 Claims, 25 Drawing Sheets

(56) References Cited

U.S. PATENT DOCUMENTS

| | | |
|---|---|---|
| 9,814,232 B2 | 11/2017 | Nakayama et al. |
| 2003/0049410 A1 | 3/2003 | Munagavalasa et al. |
| 2004/0020104 A1 | 2/2004 | Feldhege et al. |
| 2005/0005504 A1 | 1/2005 | Munagavalasa et al. |
| 2005/0089669 A1 | 4/2005 | Sobonya et al. |
| 2007/0053959 A1 | 3/2007 | Smith et al. |
| 2008/0115406 A1 | 5/2008 | Duston et al. |
| 2008/0245315 A1 | 10/2008 | Tyler |
| 2009/0067760 A1 | 3/2009 | Shelley et al. |
| 2009/0125320 A1 | 5/2009 | Bickett |
| 2010/0139861 A1 | 6/2010 | Hausen et al. |
| 2010/0323134 A1 | 12/2010 | Bostian et al. |
| 2013/0095162 A1 | 4/2013 | Quinn |
| 2014/0141051 A1 | 5/2014 | Swanson et al. |
| 2015/0072862 A1* | 3/2015 | Dujardin ............... A01N 47/36 504/215 |
| 2016/0058605 A1 | 3/2016 | Chang |
| 2016/0117957 A1 | 4/2016 | DiGregorio et al. |
| 2017/0174405 A1* | 6/2017 | Riis .................... B32B 15/20 |
| 2018/0153115 A1 | 6/2018 | Widder et al. |

FOREIGN PATENT DOCUMENTS

| | | | |
|---|---|---|---|
| WO | 0009174 A1 | 2/2000 | |
| WO | 0074490 A1 | 12/2000 | |
| WO | WO-0207512 A1 * | 1/2002 | .......... A01M 1/2044 |
| WO | 2006134353 A1 | 12/2006 | |
| WO | 2007111161 A1 | 10/2007 | |
| WO | 2008012507 A1 | 1/2008 | |
| WO | 2016143810 A1 | 9/2016 | |
| WO | 2017165476 A1 | 9/2017 | |
| WO | 2018208866 A1 | 11/2018 | |

* cited by examiner

DISPENSER AND METHOD OF USE THEREOF

CROSS REFERENCE TO RELATED APPLICATIONS

Not applicable

REFERENCE REGARDING FEDERALLY SPONSORED RESEARCH OR DEVELOPMENT

Not applicable

SEQUENCE LISTING

Not applicable

BACKGROUND OF THE INVENTION

1. Field of the Invention

The present invention relates generally to passive volatile material dispensers and, more particularly, to a multi-layer film dispenser configured to passively emanate a volatile material, such as an insecticide, a fragrance, or any other volatile material.

2. Description of the Background of the Invention

Various volatile material dispensing devices known in the art generally include a reservoir that holds a volatile material, as well as a housing or support structure that retains the reservoir. These devices typically either allow passive diffusion of the volatile material to occur without the aid of a dispensing mechanism, or enhance and/or facilitate the release of the volatile material using a dispensing mechanism. For example, typical dispensing mechanisms used in volatile material dispensing devices include a heating device and/or a fan. Such prior passive dispensers may often require these mechanisms or other costly materials that lead to more expensive dispensers.

In some instances, dispensers may be provided as a sheet or film, and may include a plurality of layers, one of which may be exposed to a surrounding environment and resultantly emanate an amount of volatile material therefrom. However, such prior passive dispensers also have common drawbacks. For one, many films or sheets used to dispense a volatile are weak structures susceptible to curling or tearing during opening or use, and some film dispensers that lack a required stability or strength, may require support structures or frames to prevent the films from curling or ripping during use. For example, in conditions of high humidity, e.g., above 80% humidity, some film dispensers may absorb moisture and begin to curl onto themselves.

Further, the delivery of a volatile material or composition from a reservoir of a dispenser may be complicated by one or more factors. For example, many dispensing devices that passively emanate a volatile material are thin films having weak structures that are susceptible to tearing, as discussed above. And, due to the weak nature of these thin films, many of these dispensing devices may curl onto themselves, which at least partially blocks the emanation of a volatile material therefrom. Further, as noted above, many dispensing devices are typically used in areas having high temperatures, often in excess of 20 degrees Celsius, and high humidity, often in excess of 80% humidity. In such conditions, many of these dispensing devices may absorb moisture and, as a result, the dispensing devices may be even more susceptible to curling and/or ripping, thereby preventing the dispensing devices from properly emanating a volatile material therefrom.

Still further, many typical dispensers have sealant layers that may be peeled away at a desired time prior to use. However, typically these seals are ineffective and, as a result, the volatile material stored therein leaches out and the life of the product shortens. For example, in some instances, high temperatures may cause instability within the film or sheet, which degrades a seal of the film and resultantly releases a volatile material stored therein.

What is needed is a dispenser that preferably overcomes one or more of these drawbacks.

SUMMARY OF THE INVENTION

In one aspect, a multi-layer article is provided. The multi-layer article includes a first non-active state and a second active state. Further, the multi-layer article includes an outer layer having a first side and a second side, an inner layer adjacent to at least a portion of the outer layer and including a volatile material, and an upper layer including a first side and a second side, the first side of the upper layer being adjacent to at least a portion of the inner layer. The multi-layer article is also folded upon itself in the first non-active state so that at least a first portion of the second side of the upper layer is disposed on a top of a second side of the upper layer, and the first portion and the second portion of the upper layer are heat sealed in the non-active state.

In some embodiments, the outer layer may include a high-density polyethylene, the inner layer may include a nylon, and the upper layer may include an ethylene vinyl acetate (EVA) with polyolefin. In further embodiments, the volatile material may comprise an active agent and a solvent. The active agent may be transfluthrin and the solvent may be a di-propylene glycol dimethyl ether, for example. Further, the multi-layer article may be initially dosed with about 110 mg of the active agent, and when in a non-active state, the multi-layer article may retain at least about 85% of the initial dosage of the active agent after two months or 60 days. In certain aspects, when the multi-layer article is in the active state, the multi-layer article may emanate the active agent at an emanation rate of between about 1 mg/day to 4 mg/day. The multi-layer article may also have a peel strength, which may be characterized by an average load strength capable of separating a heat seal between the first and second portions of the upper layer. In these embodiments, the peel strength may range between about 2 N and about 50 N. Further, the active agent and the inner layer of the multi-layer article may have a relative energy difference (or RED value) between about 0.5 and 15.

In further aspects, another multi-layer article is provided that includes a first non-active state and a second active state. Further, the multi-layer article includes an outer layer, an inner layer, and an upper layer. The outer layer is formed from a high crystalline polymer structure and has a first side and a second side. The inner layer is adjacent to at least a portion of the outer layer and includes a material selected from the group consisting of a polyethylene (linear low-density polyethylene (LLDPE), low-density polyethylene (LDPE), a high-density polyethylene (HDPE), etc.), a polyvinyl alcohol, a polypropylene, an ethylene-vinyl acetate, and an ethylene vinyl alcohol. The upper layer is adjacent to at least a portion of the inner layer and includes a material selected from the group consisting of an ethylene-vinyl acetate, a polyethylene, a polypropylene, an ethylene vinyl alcohol copolymer, a polyester, a nylon, or a butylene copolymer. Further, the upper layer includes a first side and a second side, the first side of the upper layer being adjacent to at least a portion of the inner layer, and the multi-layer article is folded upon itself in the first non-active state so that at least a first portion of the second side of the upper layer is disposed on a top of a second portion of the second side of the upper layer. Additionally, the first portion and the second portion of the upper layer are heat sealed in the non-active state, and the inner layer comprises a volatile material therein.

In further embodiments, a method of producing a multi-layer article may be provided. The method includes the steps of extruding an outer layer having a first side and a second side, extruding an inner layer adjacent to at least a portion of the extruded outer layer, extruding an upper layer adjacent to at least a portion of the extruded inner layer, dosing at least the inner layer with a volatile material, folding a first side of the dispensing device onto a second side of the dispensing device, and applying heat to the multi-layer article to hermetically seal a first portion of the upper layer to at least a second portion of the upper layer.

The foregoing and other aspects and advantages of the disclosure will appear from the following description. In the description, reference is made to the accompanying drawings, which form a part hereof, and in which there is shown by way of illustration a preferred configuration of the disclosure. Such configuration does not necessarily represent the full scope of the disclosure, however, and reference is made therefore to the claims herein for interpreting the scope of the disclosure.

BRIEF DESCRIPTION OF THE DRAWINGS

The invention will be better understood and features, aspects, and advantages other than those set forth above will become apparent when consideration is given to the following detailed description thereof. Such detailed description makes reference to the following drawings.

Figure 1:
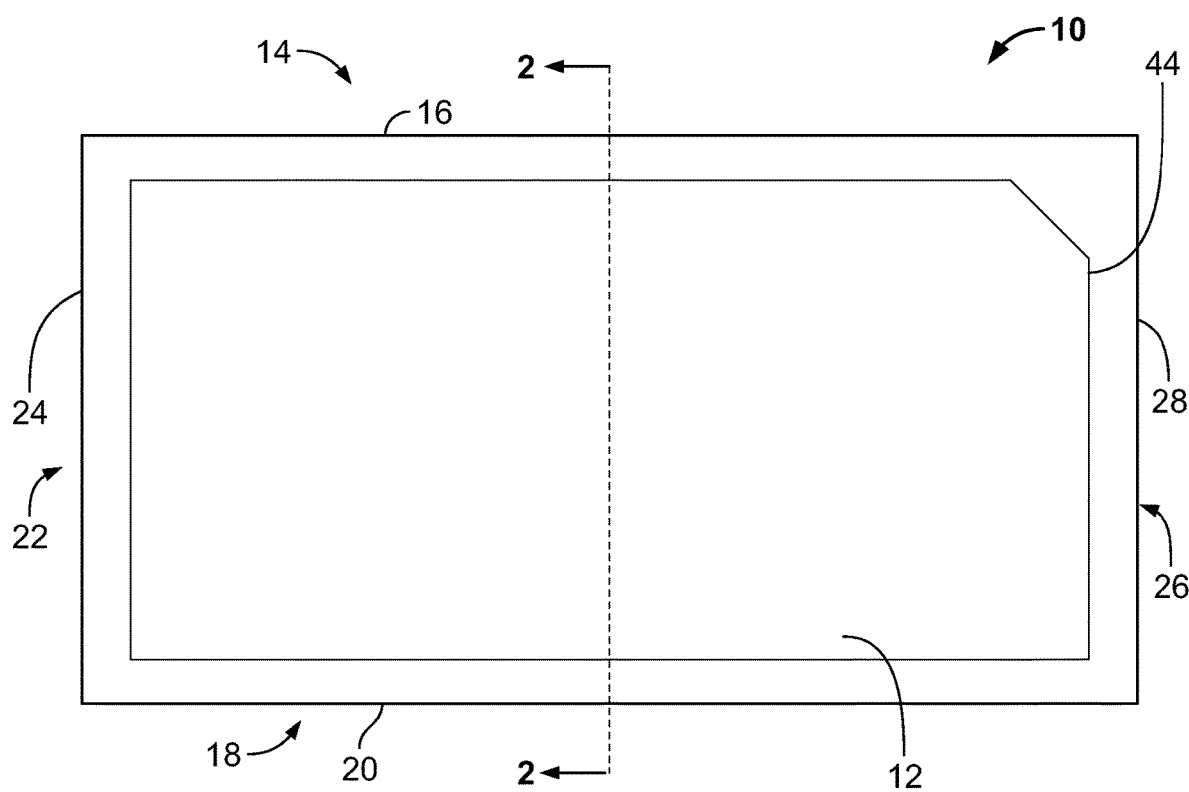
FIG. 1 is a front elevational view of a first embodiment of a dispensing device in a first state.
Figure 2:
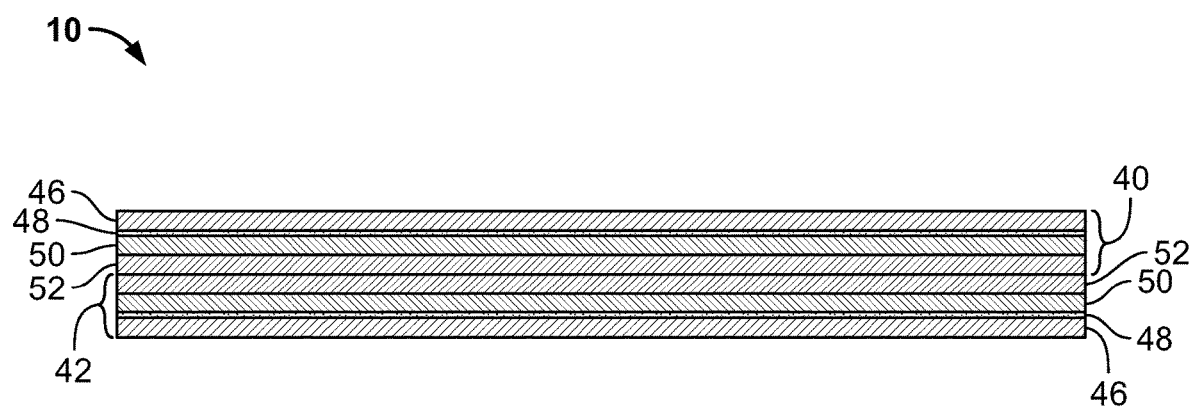
FIG. 2 is a cross-sectional view of the dispensing device of FIG. 1, taken along lines 2-2 thereof.

Before the embodiments of the disclosure are explained in detail, it is to be understood that the disclosure is not limited in its application to the details of construction and the arrangement of the components set forth in the following description or illustrated in the drawings. The disclosure is capable of other embodiments and of being practiced or being carried out in various ways. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof.

DETAILED DESCRIPTION

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures. The figures, which are not necessarily to scale, depict selected embodiments and are not intended to limit the scope of embodiments of the invention. Skilled artisans may also recognize that the examples provided herein have many useful alternatives and fall within the scope of embodiments of the invention.

In many instances, it may be useful to provide a vapor-dispensing device for either the passive or active emission of one or more volatiles into a surrounding atmosphere. In one example, it may be useful to emit a fragrance into a space such as a room or household to provide a pleasing aroma, or in another example, it may be useful to emit a pest control agent into the atmosphere to repel or eliminate a pest, such as mosquitos, flies, moths, or other insects. In yet another example, it may be useful to emit a deodorant into an environment in order to neutralize a foul odor or the like. Accordingly, many varieties and variations of vapor-dispensing devices may include a reservoir that contains a volatile composition.

Certain embodiments of the present disclosure provide a multi-layer article including a first non-active state and a second active state, the multi-layer article comprising an outer layer having a first side and a second side, an inner layer adjacent to at least a portion of the outer layer and including a volatile material, and an upper layer including a first side and a second side, the first side of the upper layer being adjacent to at least a portion of the inner layer. The multi-layer article is folded upon itself in the first non-active state so that at least a first portion of the second side of the upper layer is disposed on a top of a second portion of the second side of the upper layer, and the first portion and the second portion of the upper layer are heat sealed in the non-active state.

Referring to the drawings, FIGS. 1-6 depict a dispensing device 10 adapted to dispense a volatile material. The dispensing device 10 may include a first, closed, non-active state (see FIG. 1), a second intermediate state (see FIG. 3), and a third, open, active state (see FIGS. 4 and 5), and may generally include a multi-layer film structure and a volatile material disposed on or within the multi-layer film structure so that, during use, the dispensing device 10 is adapted to passively emanate or dispense the volatile material over a desired amount of time. As will be further discussed herein, the volatile material disposed on or within the dispensing device 10 may be any type of volatile material adapted to be dispensed into an environment. Non-limiting examples include an insecticide, a cleaner, an insect repellant, an insect attractant, a disinfectant, a mold or mildew inhibitor, a fragrance, a disinfectant, an air purifier, an aromatherapy scent, an odor eliminator, a positive fragrancing volatile material, an air-freshener, a deodorizer, or the like, or combinations thereof. In addition, additives may be included in the volatile material, such as fragrances and/or preservatives, for example.

With particular reference to FIG. 1, when in a closed state, the dispensing device 10 may include an outer layer 12 with a top side 14 having an upper edge 16, a bottom side 18 having a lower edge 20, a left side 22 having a first side edge 24, and a right side 26 having a second side edge 28. Further, although the dispensing device 10 may be generally defined as rectangular in shape, other embodiments of the dispensing device 10 may be in a variety of forms or shapes, including a square, a star, or a circle, for example.

Figure 19:
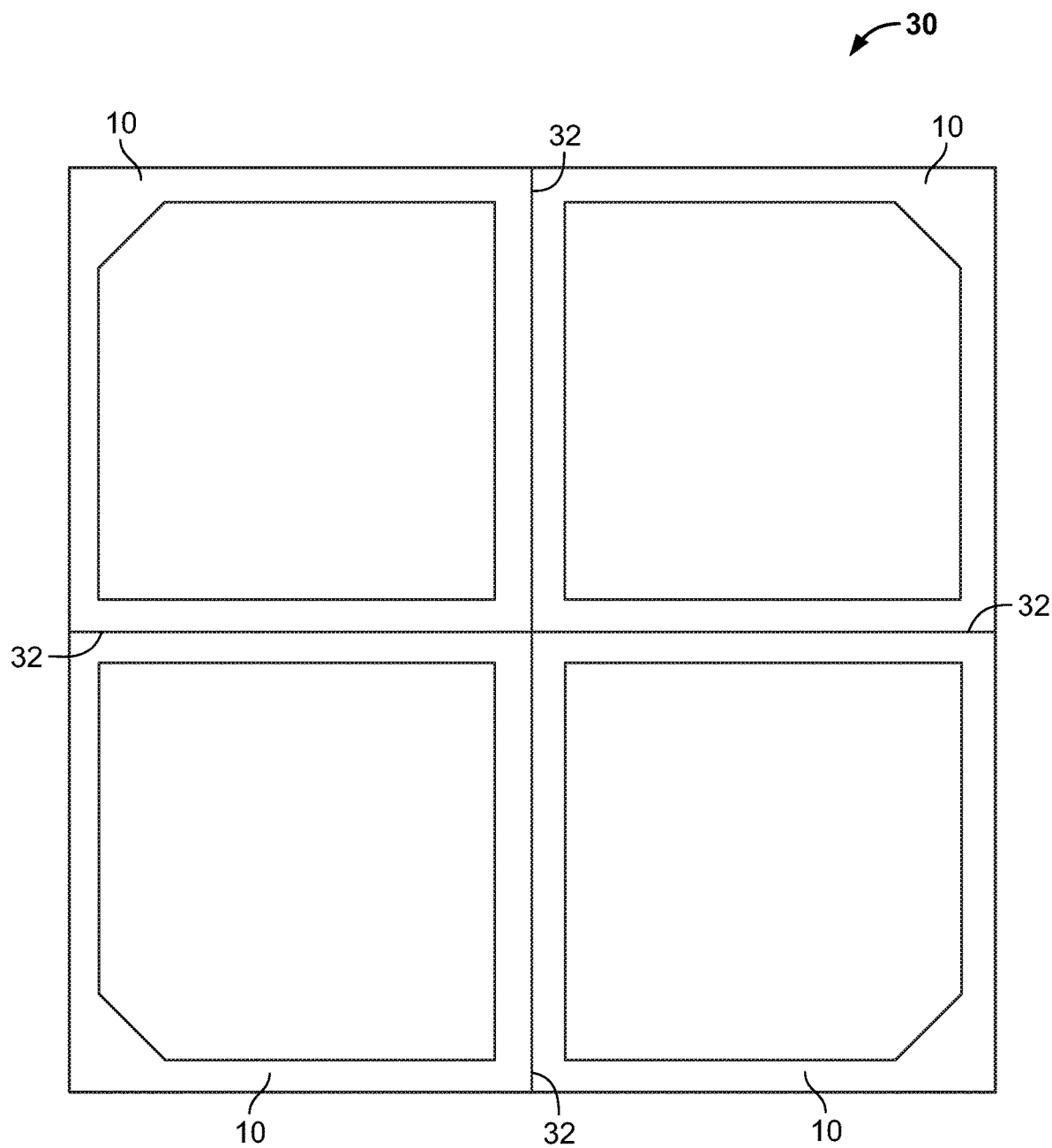
FIG. 19 is a front elevational view of a dispenser that includes a plurality of dispensing devices.
Figure 20:
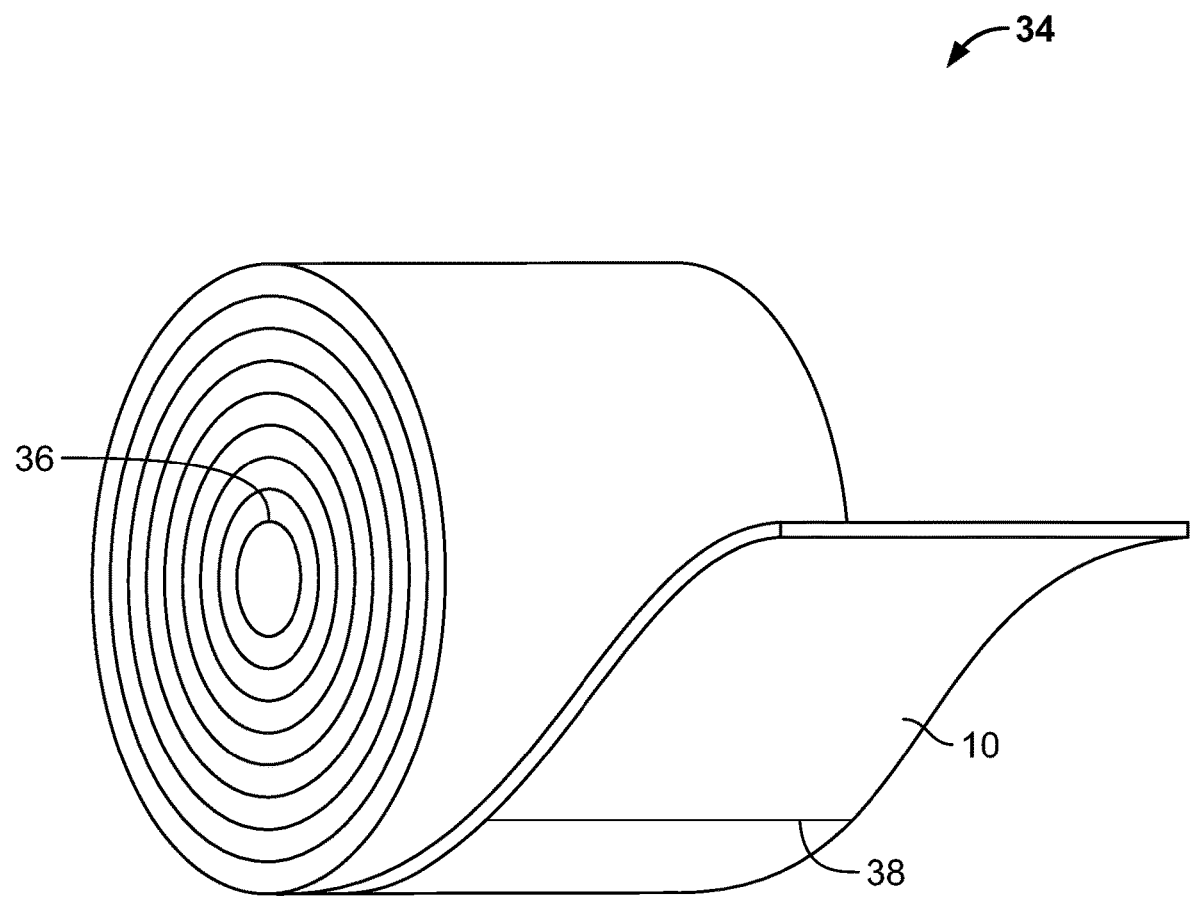
FIG. 20 is a front, top, and right isometric view of a second embodiment of a dispenser that includes a plurality of dispensing devices.

Additionally, in some embodiments, the dispensing device 10 may be provided with one or more additional dispensing devices. For example, as shown in FIG. 19, a dispenser 30 may include four dispensing devices 10. In these embodiments, the dispensing device 10 may include one or more areas of weakness or serrated sections 32, which allow the dispensing devices 10 to be individually separable from the dispenser 30. In alternative embodiments, such as that shown in FIG. 20, a dispenser 34 may include a spool 36 and a plurality of dispensing devices 10 wound thereabout. Similar to the embodiment shown in FIG. 19, the dispenser 34 may include one or more areas of weakness or serrated sections 38 between the dispensing devices 10 that allow the dispensing devices 10 to be individually separable from one another when desired or prior to use.

As will be further discussed herein, the dispensing device 10 may be constructed from one or more layers. In one embodiment, the structure of the dispensing device 10 may include a plurality of extruded layers that may be folded to produce an upper portion 40 and a lower portion 42 (see FIG. 2) and, after folding the upper portion 40 onto the lower portion 42, the upper portion 40 and the lower portion 42 may be joined together by a seal 44 (see FIG. 1). In such embodiments, the upper portion 40 and the lower portion 42 may be mirror images of one another. For example, as will be further described herein, a medial section of the dispensing device 10 may be folded along an axis to position the dispensing device 10 in a closed state so that the dispensing device 10 may include an upper portion 40 having an outer layer 46, an adhesive layer 48, an inner layer 50, and a sealant layer 52, and a lower portion 42 having the outer layer 46, the adhesive layer 48, the inner layer 50, and the sealant layer 52.

The seal 44 may extend around an interior periphery of the dispensing device 10 and, in particular embodiments, may be a hermetic heat seal that eliminates the need of an adhesive that would be otherwise required to seal the dispensing device 10. In particular, the seal 44 may extend around the dispensing device 10 and may be proximate, and/or parallel with, the upper edge 16, the lower edge 20, the first side edge 24, and the second edge 28. In some embodiments, the seal 44 may only extend along the left side 22, the top side 14, and the right side 26 of the dispensing device 10, as will be further discussed herein.

Figure 3:
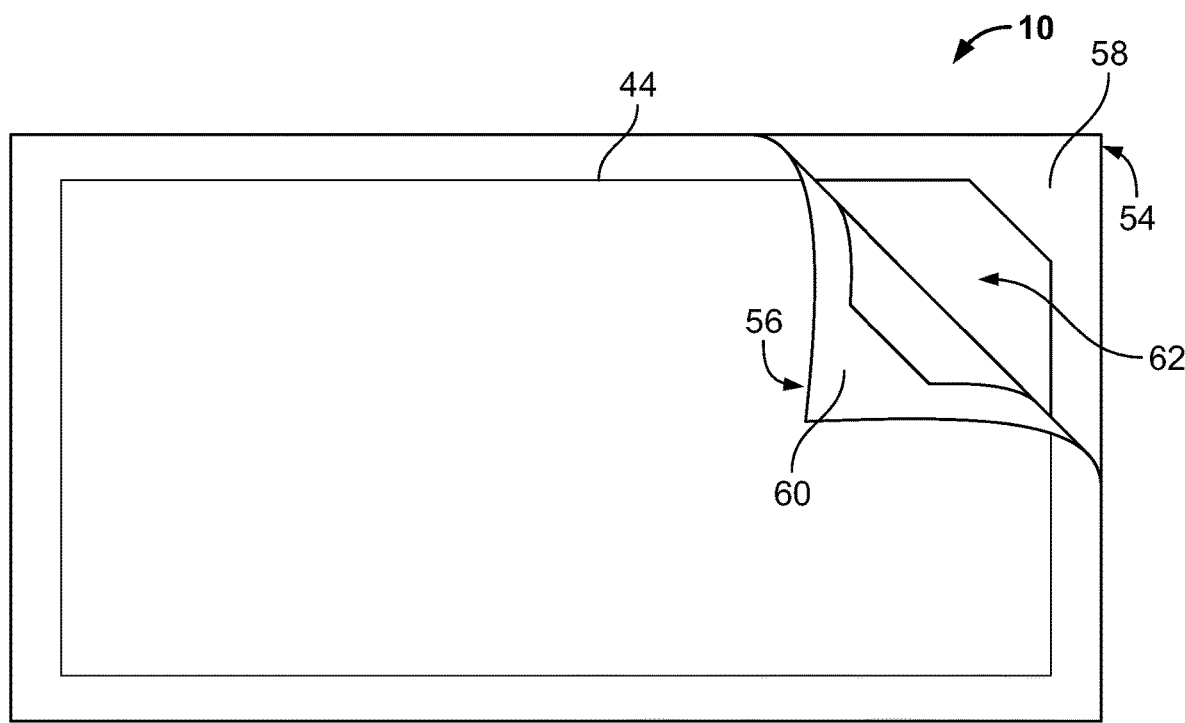
FIG. 3 is a front elevational view of the dispensing device of FIG. 1 in a second, intermediate state.

As best shown in FIG. 3, the dispensing device 10 may be opened by a user pulling apart the dispensing device 10 at corners 54, 56. In this embodiment, the corners 54, 56 include tabbed sections 58, 60 that allow a user to apply a pulling force to the corners 54, 56 and, as a result, allow the corners 54, 56 to be easily parted to open the dispensing device 10. A user may continue to pull apart the dispensing device 10 until the dispensing device 10 is completely unfolded, such as in FIGS. 4 and 5. Upon opening the dispensing device 10, an interior 62 of the dispensing device 10 may be exposed and, as will be further discussed herein, a volatile material may emanate therefrom.

Figure 7:
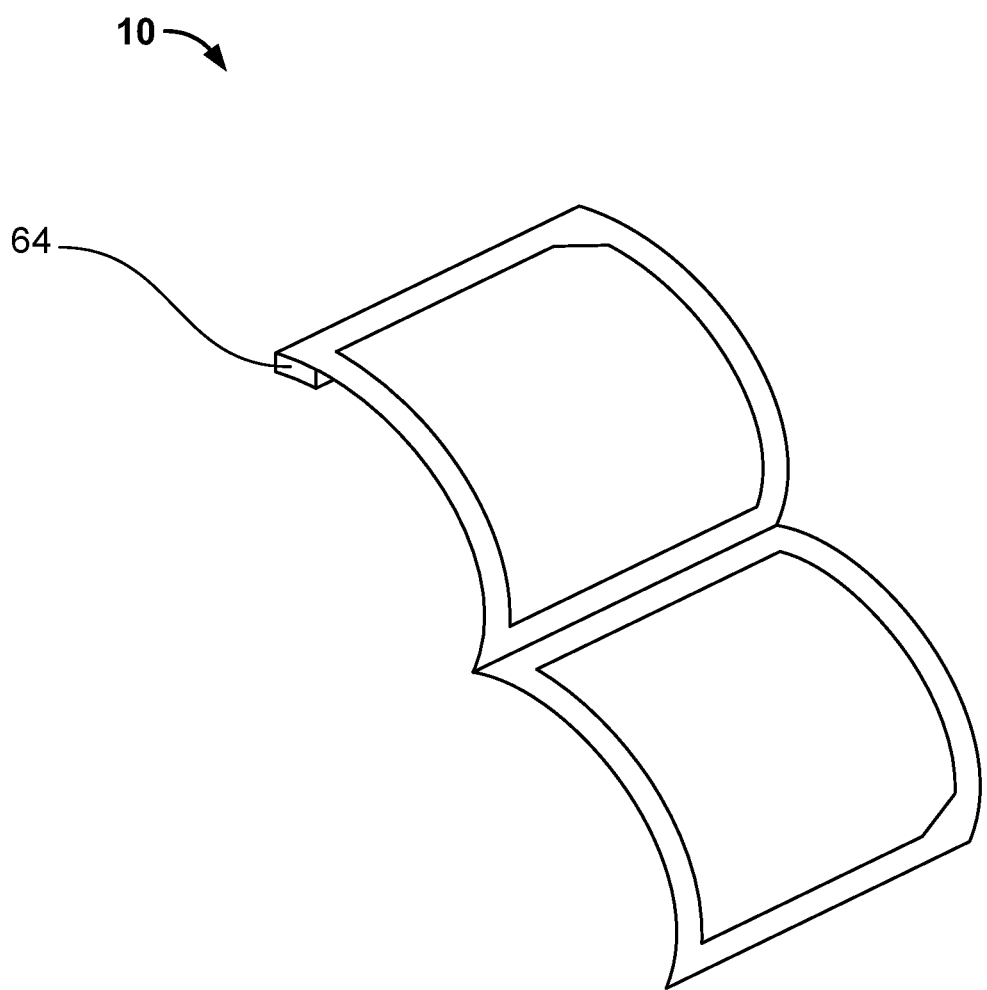
FIG. 7 is an isometric view of the dispensing device of FIG. 1 in a third state, according to a second aspect.
Figure 8:
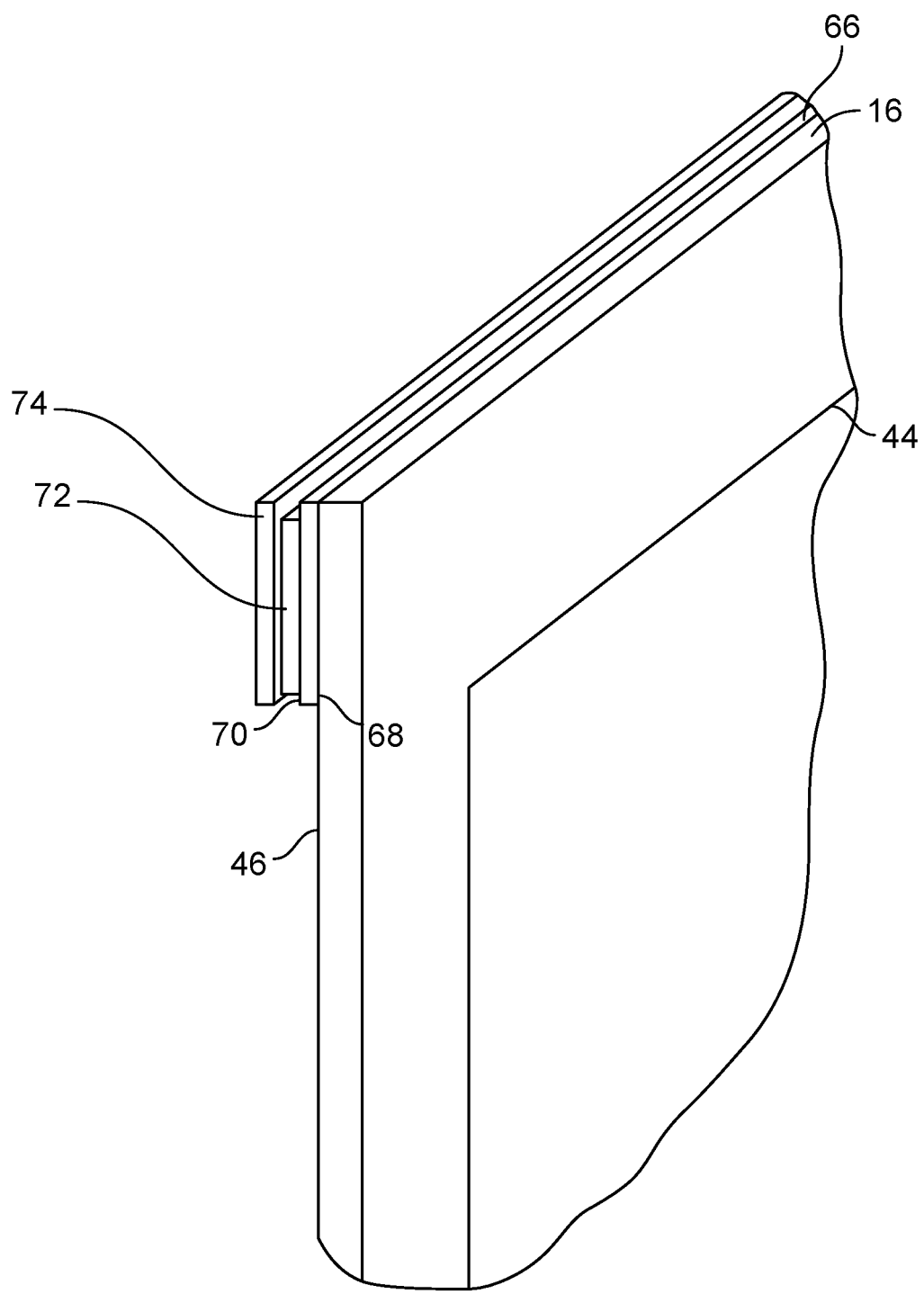
FIG. 8 is an enlarged fragmentary isometric view of the dispensing device of FIG. 7.
Figure 9:
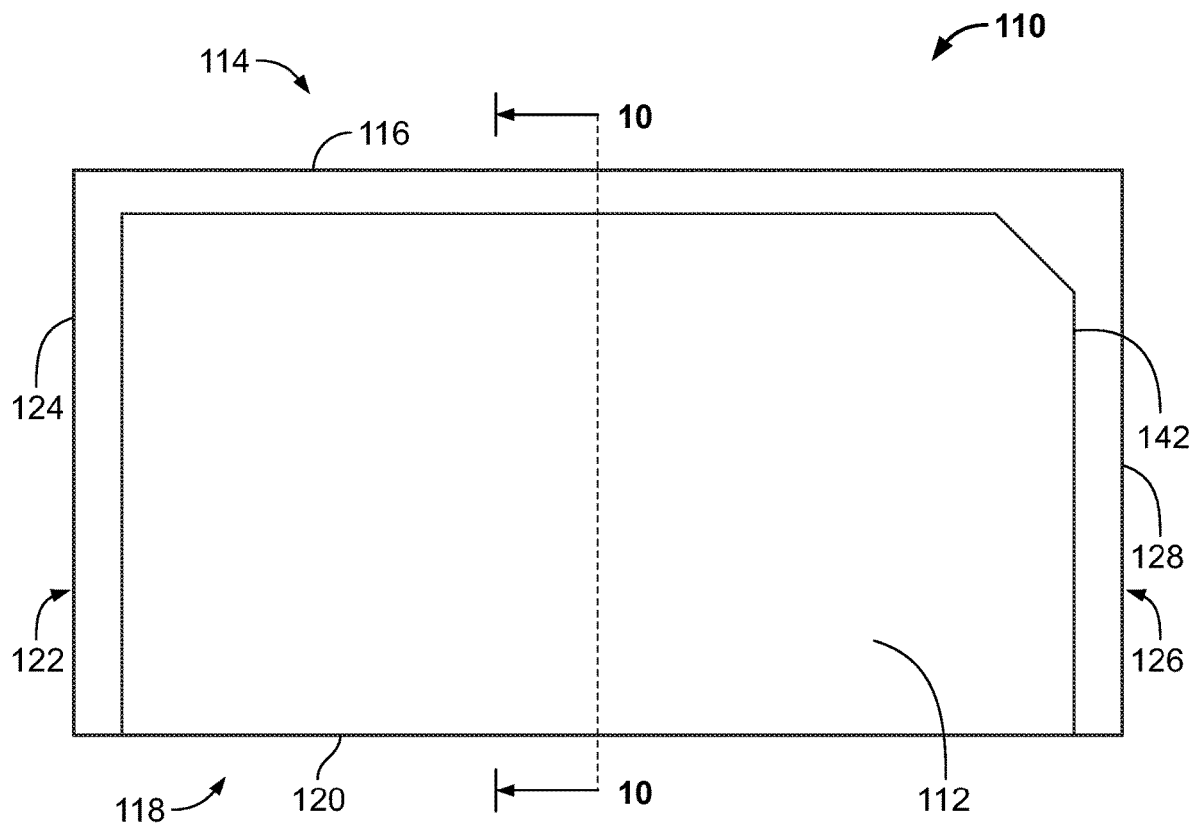
FIG. 9 is a front elevational view of a second embodiment of a dispensing device in a first state.
Figure 10:
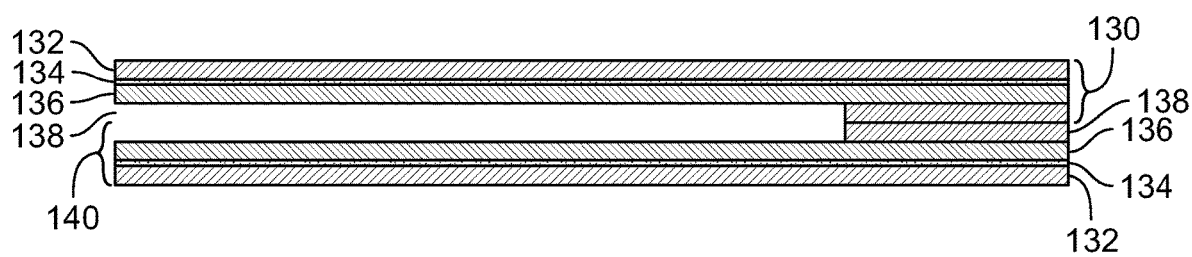
FIG. 10 is a fragmentary cross-sectional view of the dispensing device of FIG. 9, taken along lines 10-10 thereof.

FIGS. 7 and 8 illustrate the dispensing device 10 according to a second aspect of the present embodiment. In this particular aspect, a mounting element 64 may be affixed to the dispensing device 10 on a rear surface of the outer surface 46. For example, as shown in FIGS. 7 and 8, the mounting element 64 may be affixed to the dispensing device 10 on a rear edge of the outer surface 46 proximate an upper edge 16 of the dispensing device 10.

In one embodiment, as shown in FIG. 8, the mounting element 64 may be a double-sided tape 66 having first and second adhesive sides 68, 70, the first adhesive side 68 being adhered to the outer surface 46 of the dispensing device 10 and the second adhesive side 70 may be adhered to a surface (not shown), which will be further discussed herein. Exemplary embodiments of a mounting element 64 that may be used with the dispensing device 10 are disclosed in U.S. Patent Publication No. 2005/0005504 A1, the entirety of which is incorporated by reference herein.

Such double-sided tapes are available from the Minnesota Mining & Manufacturing Company (i.e., 3M) such as 3M's repositionable Tape 9415PC or Tape 9425PC. The first adhesive side 68 may remain firmly affixed to the dispensing device 10 and the second adhesive side 70 may be affixed to a number of surfaces, such as windows, walls, doors, furniture, or other surfaces. While the dispensing device 10 may be attached to a surface using the mounting element 64, as shown in this embodiment, the dispensing device 10 may be attached to a surface using alternative suitable means of mounting or hanging.

The dispensing device 10 may also further include a use-up cue 72 (see FIG. 8) that indicates to a user that the dispensing device 10 has volatized all or nearly all of the volatile liquid therefrom. For example, the use-up cue 72 may be a color change sticker, which may include a liner 74 that is removed by a user at or about the same time the dispensing device 10 is opened or transitions between a non-active state or active state. In this embodiment, when the liner 74 is removed, the use-up cue 72 may display a first color, e.g., red, and after a predetermined time, at or near full volatilization of a volatile material from the dispensing device 10, the use-up cue 72 changes to a second color, e.g., green, indicating to a user that the useful life of the dispensing device 10 has expired. The use-up cue 72 may also incorporate text, such as the word "discard" that would appear after a predetermined amount of time and the text signals to the user that the useful life of the dispensing device 10 has expired. Stickers employing this general type of color change technology are available from Temtec, a division of Brady Worldwide, Suffern, New York, 10901, USA, and may be marketed under the mark TEMPbadge®.

While a color change sticker may be used as the use-up cue 72, any other suitable form of use-up cue or indicator may be used. For example, the liquid volatile could incorporate a fragrance, such as a floral or citrus scent, that becomes less odorous over time. At or near full volatilization, the fragrance is not detectable by the average user signaling the need for replacement of the dispensing device 10. The liner 74 may also be used to line the double-sided tape 66 and peeling the liner 74 may expose the second adhesive side 70.

Figure 11:
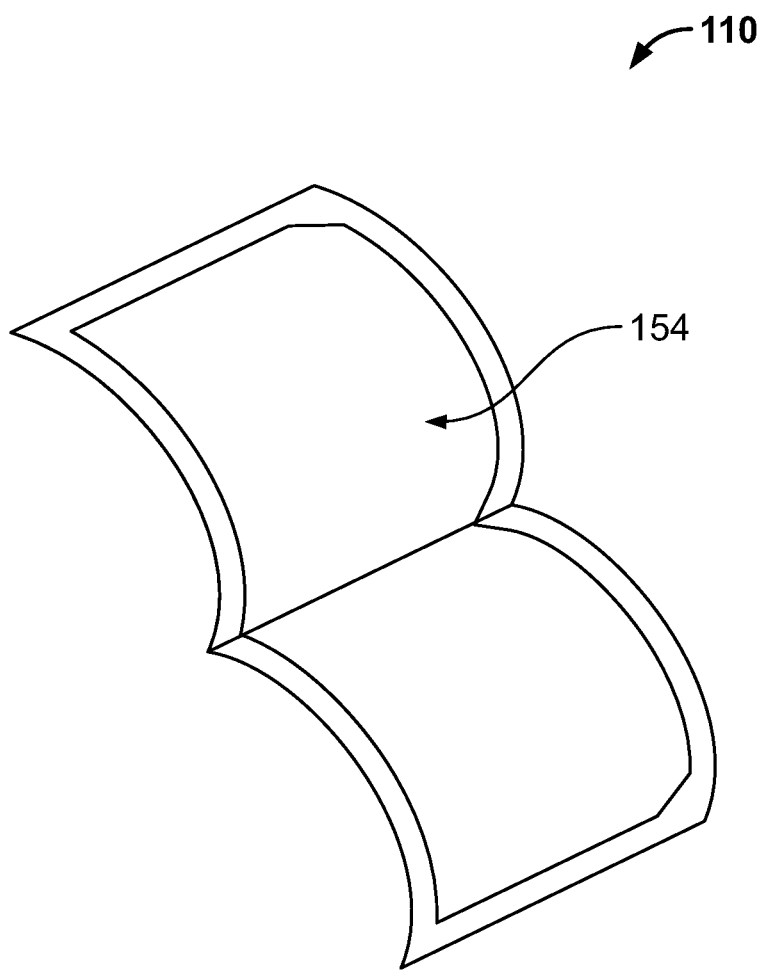
FIG. 11 is an isometric view of the dispensing device of FIG. 9 in a second state.
Figure 12:
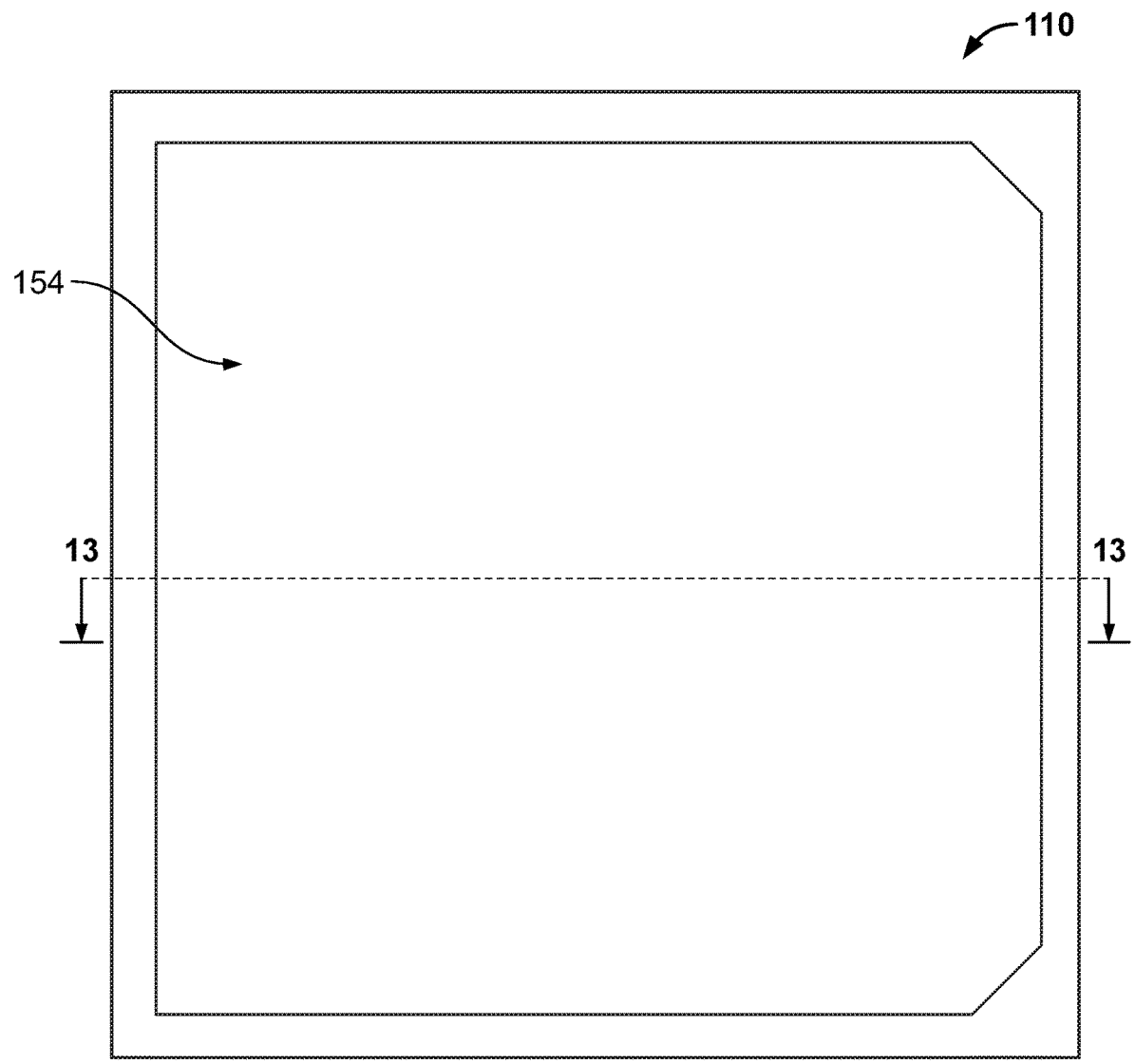
FIG. 12 is a front elevational view of the dispensing device of FIG. 11.
Figure 13:
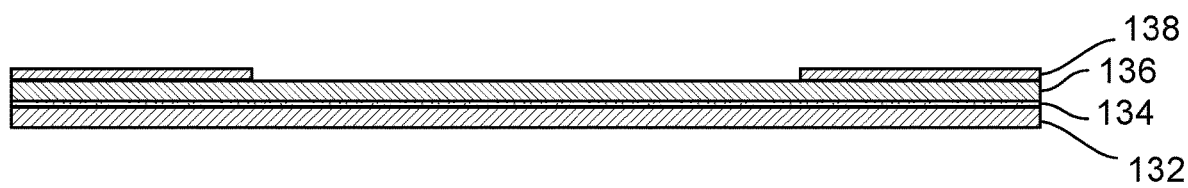
FIG. 13 is a fragmentary cross-sectional view of the dispensing device of FIG. 12, taken along lines 13-13 thereof.

Turning to FIGS. 9-13, in a second embodiment, a dispensing device 110 may include a closed state (see FIG. 9) and an open state (see FIGS. 11 and 12). Similar to the dispensing device 10, the dispensing device 110 generally includes a multi-layer film structure and a volatile material disposed on or within the multi-layer film structure so that, during use, the dispensing device 110 may be adapted to passively emanate or dispense the volatile material therefrom over a desired amount of time.

Referencing FIGS. 9-13, when in a closed state, the dispensing device 110 may include an outer layer 112 with a top side 114 having an upper edge 116, a bottom side 118 having a lower edge 120, a left side 122 having a first side edge 124, and a right side 126 having a second side edge 128. Further, in this embodiment, the structure of the dispensing device 110 is formed from an upper portion 130 having an outer layer 132, an adhesive layer 134, an inner layer 136, and a sealant layer 138, and a lower portion 140 having the outer layer 132, the adhesive layer 134, the inner layer 136, and the sealant layer 138. However, in this particular embodiment, the sealant layer 138 is disposed on top of and proximate an outer periphery of the inner layer 136.

As will be further discussed herein, the dispensing device 110 may be constructed from one or more layers. In one embodiment, the structure of the dispensing device 110 may include a plurality of extruded layers that may be folded to produce the upper portion 130 and the lower portion 140 (see FIG. 10) and, after folding the upper portion 130 onto the lower portion 140, the upper portion 130 and the lower portion 140 may be joined together by a seal 142 (see FIG. 9). In such embodiments, the upper portion 130 and the lower portion 140 may be mirror images of one another. For example, as will be further described herein, a medial section of the dispensing device 110 may be folded along an axis to position the dispensing device 110 in a closed state so that the dispensing device 110 may include the upper portion 130 having the outer layer 132, the adhesive layer 134, the inner layer 136, and the sealant layer 138, and the lower portion 140 having the outer layer 132, the adhesive layer 134, the inner layer 136, and the sealant layer 138.

The seal 142 may extend around an interior periphery of the dispensing device 110 and, in particular embodiments, may be a hermetic heat seal that eliminates the need of an adhesive that would be otherwise required to seal the dispensing device 110. More particularly, the seal 142 may extend only along the left edge 122, the top side 114, and the right side 125 of the dispensing device 110, when the dispensing device 110 is in a closed state. Similarly, the sealant layer 138 may extend only along the left edge 122, the top side 114, and the right side 125 of the dispensing device 110, when the dispensing device is in a closed state.

Figure 14:
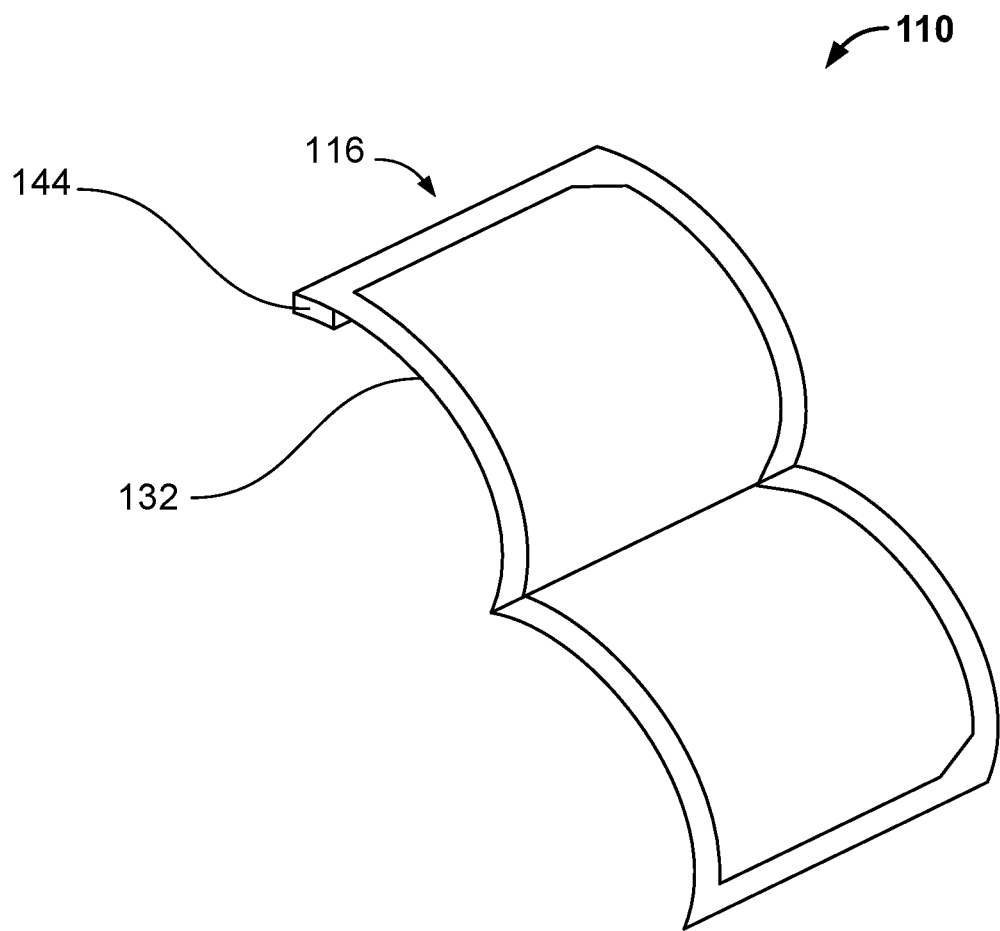
FIG. 14 is an isometric view of the dispensing device of FIG. 9 in a third state, according to a second aspect.

FIG. 14 illustrates the dispensing device 110 according to a second aspect of the present embodiment. In this particular aspect, similar to the dispensing device 10 depicted in FIGS. 7 and 8, a mounting element 144 may be affixed to the dispensing device 110 on a rear surface of the outer layer 132. For example, as shown in FIG. 14, the mounting element 144 may be affixed to the dispensing device 110 on a rear edge of the outer layer 132 proximate an upper edge 116 of the dispensing device 110. Further, similar to the dispensing device 10 depicted in FIGS. 7 and 8, the mounting element 144 may be a double-sided tape having first and second adhesive sides, the first adhesive side being adhered to the outer layer 132 of the dispensing device 110 and the second adhesive side may be adhered to a surface, as previously discussed herein. As also previously discussed herein, exemplary embodiments of a mounting elements 62, 144 that may be used with the dispensing devices 10, 110 are disclosed in U.S. Patent Publication No. 2005/0005504 A1, the entirety of which is incorporated by reference herein.

Outer Layer

The outer layer 46, 132 may be formed using one or more materials to provide sufficient support and strength to the dispensing device 10, 110. Additionally, the materials used to form the outer layer 46, 132 may provide the dispensing device 10, 110 with a high-tensile strength that prevents the dispensing device 10, 110 from curling or ripping when either in the closed, non-active state or in the open, active state. Even further, the outer layer 46, 132 may be formed from one or more materials that are non-permeable to the volatile material positioned within the dispensing device 10, 110. The outer layer 46, 132 may also be printed or colored to improve the aesthetics of the dispensing device 10, 110.

In some embodiments, the outer layer 46, 132 may include one or more layers. For example, the outer layer 46, 132 may be homogenous, i.e., a single layer, or a composite material comprising a mixture of one or more materials and/or one or more layers. The outer layer 46, 132 may be formed to provide the dispensing device 10, 110 with a desired or required structural integrity, and the one or more materials of the outer layer 46, 132 may be selected to provide mechanical stability to the dispensing device 10, 110 or mechanical stability to the one or more additional layers or components of the dispensing device 10, 110, e.g., the inner layer 50, 136, the sealant layer 52, 138, the adhesive layer 48, 134, and/or the volatile material. Factors that may influence the selection of the materials for the outer layer 46, 132 may include mechanical, chemical resistance, or thermal properties of one or more materials of the outer layer 46, 132. As will be further discussed herein, the dispensing device 10, 110 may be hung or attached to a surface using one or more points of contact and, as such, it is desired that the outer layer 46, 132 provide ample mechanical support to the dispensing device 10, 110 when hung or attached to a surface.

The outer layer 46, 132, and the one or more materials thereof, has a high mechanical stability and a high mechanical strength during conditions of high humidity and high temperatures. In one aspect, one or more materials of the outer layer 46, 132 may be characterized by a stiffness value, such as a tensile modulus, a Young's modulus, or a modulus of elasticity. For example, a material of the outer layer 46, 132 may have a Young's modulus of elasticity ranging between about 0.5 GPa and about 5 GPa, or between about 0.8 GPa and about 3 GPa, or between about 1 GPa and about 2.5 GPa.

The surface characteristics may also contribute to the selection of the material(s) for the outer layer 46, 132. For example, the polarity or roughness of the surface of the outer layer 46, 132 may contribute to the effectiveness of the outer layer 46, 132 to bond with, adhere to, or otherwise couple to the other layers of the dispensing device 10, 110, such as the inner layer 50, 136. Additional characteristics of the outer layer 46, 132 that may influence the adhesion of the outer layer 46, 132 to another layer, e.g., the inner layer 50, 136, as well as porosity, surface energy, and hydrophilicity.

The outer layer 46, 132 may have a flow resistance that is higher than any other layer of the dispensing device 10, 110. Put differently, the outer layer 46, 132 may have a porosity that is lower than a porosity of the inner layer 50, 136 and/or the sealant layer 52, 138. For example, the outer layer 46, 132 may be a polymer-based material that is substantially closed or non-porous and, in particular, non-porous to the volatile material of the dispensing device 10, 110.

The outer layer 46, 132 may be formed partially or entirely from a high crystalline polymer structure, such as a high-density polyethylene (HDPE) or a polyester (polyethylene terephthalate (PET), or a polybutylene terephthalate (PBT)), or engineered plastics that provide the dispensing device 10, 110 with an increased stiffness, and more particularly, an increased stiffness at high temperatures and high humidity. As a result, the outer layer 46, 132 may ensure that the dispensing device 10, 110 remains flat and uncurled when in an open state, thereby allowing the volatile material to continuously emanate therefrom. In addition, the outer layer 46, 132 provides enough support to the dispensing device 10, 110, so that a secondary structure, e.g., a frame, may not be required to keep the dispensing device 10, 110 open and ensure the interior 62 is exposed to the ambient environment. However, in some embodiments, a secondary structure may still be desired and may be included with the dispensing device 10, 110.

In additional embodiments, the outer layer 46, 132 may include a polyoxymethylene (POM), also known as an acetal, polyacetal, or polyformaldehyde, and/or a synthetic polymer, such as a nylon, including nylon 66, nylon 6, nylon 11, nylon 46, nylon 510, or nylon 1,6. In further embodiments, the outer layer 46, 132 may include a polytetrafluoroethylene (PTFE), an isotactic polypropylene, a high-density polyethylene (HDPE) or polyethylene high-density (PEHD), or a low-density polyethylene (LDPE), Polyethylene naphthalate Copolymer (PET-PEN), Polyvinyl chloride PVC or Polyvinylidene chloride, PVDC or metallized aluminum.

The outer layer 46, 132 may be a relatively thin layer with a thickness ranging between about 10 μm (0.00001 m) and about 250 μm (0.00025 m). In other embodiments, a thickness of the outer layer 46, 132 may range between about 50 μm and about 100 μm, or between about 75 μm and about 90 μm. An outer layer 46, 132 having a thickness of at least 10 μm may be required to maintain the mechanical integrity of the outer layer 46, 132 and, resultantly, the mechanical integrity of the dispensing device 10, 110.

Inner Layer

The inner layer 50, 136 may be provided on top of the outer layer 46, 132 and may be adhered thereto using the adhesive layer 48, 134, as will be further discussed herein. The inner layer 50, 136 may also contain the volatile material therein and may be a reservoir in which the volatile material is stored. Further, the inner layer 50, 136 may include at least one or more materials that act as a barrier layer to the volatile material stored therein. That is, the inner layer 50, 136 may include at least one or more materials configured to be rate-limiting for mass-transport of the volatile material from the dispensing device 10, 110. For example, the inner layer 50, 136 may be a barrier layer formed by one or more materials that are permeable to the volatile material, as well as rate-limiting to the volatile material. In other words, the inner layer 50, 136 may be compatible with the volatile material such that the volatile material is readily stored within the inner layer 50, 136 when the dispensing device 10, 110 is in the non-active state, yet also allows for emanation of the volatile material and, in particular, emanation of the active agent within the volatile material from the dispensing device 10, 110 after the dispensing device 10, 110 transitions to the active state. As such, the inner layer 50, 136 may control the emanation rate or rate of evaporation of the volatile material from the inner layer 50, 136 and, resultantly, the emanation rate or rate of evaporation of the volatile material from the dispensing device 10, 110.

As further discussed herein, it was surprisingly or unexpectedly determined that an optimal combination or selection of the inner layer 50, 136 and the sealant layer 52, 138 may provide a dispensing device 10, 110 with the capability of containing a high dosage of an active agent or a volatile material within the dispensing device 10, 110 in a stable environment, i.e., an environment that retains substantially all of an initial dosage of an active agent or volatile material in the dispensing device 10, 110 for a prolonged period of time (e.g., two to twelve weeks, and above) when in the closed, non-active state. In such embodiments, due to a possibility of providing an initial dosage at a higher concentration and due to the capability of the inner layer 50, 136 and the sealant layer 52, 138 to retain substantially all of the initial dosage of the volatile material within the dispensing device 10, 110, the dispensing device 10, 110 may last longer periods of time or may be capable of emanating the active agent or volatile material from the dispensing device 10, 110 for periods up to and exceeding 30 days, or a month, or for periods up to and exceeding 60 days, or two months.

In one aspect, the inner layer 50, 136 includes at least one material capable of storing the volatile material therein. For example, the inner layer 50, 136 may include one or more materials adapted to dissolve or partially dissolve the volatile material to be used with the dispensing device 10, 110, which will be discussed in further detail herein. In particular embodiments, the solubility of a volatile material within the one or more layers may be characterized by Hansen solubility parameters based on three Hansen parameters: the energy from dispersion forces between molecules ($\delta_d$), the energy from dipolar intermolecular forces between molecules ($\delta_p$), and the energy from hydrogen bonds between molecules ($\delta_h$). These three parameters can be treated as coordinates for a point in the three dimensions, also known as the Hansen space, and the nearer two molecules are in this three-dimensional space, the more likely the two molecules will dissolve into each other. In order to calculate a distance (Ra) between Hansen parameters in a Hansen space, the following formula may be used:

$$(Ra)^2 = 4(\delta_{d2}-\delta_{d1})^2 + (\delta_{p2}-\delta_{p1})^2 + (\delta_{h2}-\delta_{h1})^2 \quad \text{(Eq. 1)}$$

where $\delta_{d1}$ and $\delta_{d2}$ are the dispersion parameters for the first and second molecules, respectively, $\delta_{p1}$ and $\delta_{p2}$ are the dipolar intermolecular force parameters for the first and second molecules, respectively, and $\delta_{h1}$ and $\delta_{h2}$ are the hydrogen bond parameters for the first and second molecules, respectively.

Given the parameters of each molecule or component, a distance (Ra) value may be calculated, as well as a radius value ($R_o$), and an Relative Energy Difference (RED) value may be determined according to Eq. 2:

$$RED = \frac{Ra}{R_o} \quad \text{(Eq. 2)}$$

Based on the Hansen solubility parameters and a Relative Energy Difference, an ideal combination between the one or more layers of the inner layer 50, 136 and the volatile material may be determined. For example, in some embodiments, the one or more layers of the inner layer 50, 136, individually or in combination, and the volatile material may have an RED value of less than or equal to 1. In specific embodiments, the one or more materials of the inner layer 50, 136, individually or in combination, and the volatile material or active agent within the volatile material may have an RED value greater than 5, greater than 10, greater than 15, or greater than 20.

In other embodiment, the one or more layers of the inner layer 50, 136, individually or in combination, may be characterized by their Ra value. In some embodiments, the one or more materials of the inner layer 50, 136, individually or in combination, and the volatile material or active agent within the volatile material may have a Ra value between 5 and 15, or between 6 and 14, or between 7 and 13, or between 8 and 12. For example, in one specific embodiment, a material of the inner layer 50, 136 may be ethylene vinyl acetate and the active agent of the volatile material may be transfluthrin. In this embodiment, the ethylene vinyl acetate and transfluthrin may have a Ra value between about 8 and 9, or about 8.4. In another specific embodiment, a material of the inner layer 50, 136 may be polyethylene terephthalate (PET) and the active agent of the volatile material may be transfluthrin, and the polyethylene terephthalate (PET) and transfluthrin may have a Ra value between about 11 and 13, or about 12.

Examples of materials that are satisfactory for forming the inner layer 50, 136 include a nylon or a nylon-based film, a polysulfone (PSU), an acrylonitrile butadiene styrene (ABS), a styrene-acrylonitrile (SAN), a polyethylene (PE), a poly(p-phenylen oxide) (PPO), a polybutylene terephthalate (PBT), a polyvinyl chloride (PVC), a mylar, a polycarbonate (PC), a styrene-butadiene (SBR), a polyethylene terephthalate glycol (PETG), a poly(methyl methacrylate) (PMMA), a polyvinyl alcohol (PVOH), a polystyrene (PS), a polypropylene (PP), a polyethylene terephthalate (PET), a polyethylene terephthalate/polyethylene naphthalate copolymer (PET-PEN), an ethylene-vinyl acetate (EVA), a poly (ether sulfones) (PES), an acrylonitrile-methyl acrylate copolymer (e.g., Barex® 210), a high-density polyethylene (HDPE), an ethylene vinyl alcohol (EVOH), a polyacetal or a polyoxymethylene (POM), a polyethylene glycol (PEO), a ethylene (meth)acrylic acid (EAA, EMAA) (e.g., Surlyn®), a cellophane, and/or polyacrylonitrile (PAN), and/or a combination or metalized form thereof.

In one aspect, the inner layer 50, 136 may be formed from a polyethylene (PE), a polyvinyl alcohol (PVOH), a polypropylene (PP), an ethylene-vinyl acetate (EVA), such as an ethylene-vinyl acetate resin under the trade name Elvax®, a high-density polyethylene (HDPE), and/or an ethylene vinyl alcohol (EVOH) or blends of these materials. The inner layer 50, 136 may be formed of EZ Peel® EVA or PE co-extruded sealant.

The inner layer 50, 136 may be a relatively thin layer with a thickness ranging between about 10 μm and about 250 μm, or between about 50 μm and about 100 μm, or between about 75 μm and about 90 μm.

Sealant Layer

The sealant layer 52, 138 may be provided on at least a portion of the inner layer 50, 136, as will be further discussed herein, and may be formed by one or more materials that allow the dispensing device 10, 110 to be peeled open easily or peeled open with a low grip strength.

Further, in one embodiment, the sealant layer 52, 138 may be formed by one or more materials that are non-permeable to the volatile material, or one or more materials that do not dissolve the volatile material therein. As such, the sealant layer 52, 138 may be formed by one or more materials that act as a barrier to the volatile material and prevent emanation of the volatile material from the dispensing device 10, 110 in a non-active state. Further, the sealant layer 52, 138 may contain one or more materials capable of retaining a volatile material and may be configured to be rate-limiting for mass-transport of the volatile material from the dispensing device 10, 110. In these embodiments, the sealant layer 52, 138 may also control the emanation rate or rate of evaporation of the volatile material from the dispensing device 10, 110.

In these embodiments, the sealant layer 52, 138 may also control the emanation rate or rate of evaporation of the volatile material from the dispensing device 10, 110 and, similar to the inner layer 50, 136, the compatibility of the sealant layer 52, 138 and a volatile material stored therein may be characterized by Hansen solubility parameters, a Ra value, and a Relative Energy Difference. For example, in some embodiments, the one or more layers of the sealant layer 52, 138, individually or in combination, and the volatile material or the active agent thereof may have an RED value of greater than or equal to 1. In some embodiments, the one or more materials of the sealant layer 52, 138, individually or in combination, may have an RED value greater than 1, greater than 2, or greater than 5. In such embodiments, the sealant layer 52, 138 is a material that does not dissolve the volatile material or the active agent therein. As such, in these particular embodiments, the sealant layer 52, 138 is not permeable to the volatile material and/or the active agent therein, and provides a seal that contains the volatile material and the active agent within the dispensing device 10, 110 during a non-active state.

In other embodiments, the sealant layer 52, 138 may be formed by one or more materials that are permeable to the volatile material, or one or more materials that dissolve the volatile material therein. As such, in some aspects, some materials of the sealant layer 52, 138 may act as a reservoir for a volatile material stored therein. In these embodiments, the compatibility of the sealant layer 52, 138 and a volatile material stored therein may be characterized by Hanson solubility parameters, a Ra value, and/or a Relative Energy Difference. For example, in some embodiments, one or more layers of the sealant layer 52, 138 individually or in combination, and the volatile material or the active agent may have an RED value of less than or equal to 1. In some embodiments, the one or more materials of the sealant layer 52, 138, individually or in combination, may have an RED value less than 1, or less than 0.90, or less than 0.80, or less than 0.70, or less than 0.60, or less than 0.50.

Further, in some aspects, one material of the sealant layer 52, 138 and the volatile material or the active agent may have an RED value of less than 1, less than 0.90, less than 0.80, less than 0.70, less than 0.60, or less than 0.50. And one other material of the sealant layer 52, 138 and the volatile material or the active agent may have an RED value of greater than 1, greater than 2, greater than 5, greater than 10, greater than 15, or greater than 20.

In other embodiments, the one or more layers of the sealant layer 52, 138, individually or in combination, may be characterized by their Ra value. In some embodiments, the one or more materials of the sealant layer 52, 138, individually or in combination, and the volatile material or active agent within the volatile material may have a Ra value between 5 and 15, or between 6 and 14, or between 7 and 13, or between 8 and 12. For example, in one specific embodiment, a material of the sealant layer 52, 138 may be ethylene vinyl acetate and the active agent of the volatile material may be transfluthrin. In this embodiment, ethylene vinyl acetate and transfluthrin may have a Ra value between about 11 and 13, or about 12. Further, in this embodiment, the ethylene vinyl acetate and transfluthrin may have an RED value between 2 and 3, or less than 5. In another specific embodiment, a material of the sealant layer 52, 138 may be polyethylene terephthalate (PET) and the active agent of the volatile material may be transfluthrin, and the polyethylene terephthalate (PET) and transfluthrin may have a Ra value between about 11 and 13, or about 12.

In further embodiments, which will be further discussed herein, the one or more materials of the sealant layer 52, 138 may be chosen to be capable of forming a hermetic heat seal, such as the seal 44. In particular embodiments, the sealant layer 52, 138 is composed of one or more materials capable of forming a hermetic heat seal to a second layer of the dispensing device 10, 110 and, in particular, capable of forming a hermetic heat seal to a second portion of the sealant layer 52, 138. The hermetic heat seal, as described herein, may provide the dispensing device 10, 110 with a sufficient seal capable of retaining one or more volatile materials stored therein. In addition, the hermetic heat seal may eliminate the need for an additional adhesive or chemical bond typically required to seal a film-based material.

Typically, materials capable of retaining an active agent or a volatile material, such as an insecticide, are incapable of forming a hermetic heat seal that peel easily, or vice-versa, materials capable of forming sufficient hermetic seals are not expected to adequately store or retain a volatile material. However, as shown herein, the surprising discovery has been made that some materials capable of retaining volatile insecticides (e.g., transfluthrin or metofluthrin) may also form hermetic heat seals that sufficiently retain volatile materials.

In addition to being capable of forming a heat seal, the sealant layer 52, 138 may also be composed of one or more materials that are inactive to the volatile material and, in particular, one or more materials that are inactive to the volatile material at conditions of high humidity, e.g., conditions with a humidity greater than 80%, and elevated temperatures, e.g., temperatures above 20 degrees Celsius, or 40 degrees Celsius, or 60 degrees Celsius.

Figure 4:
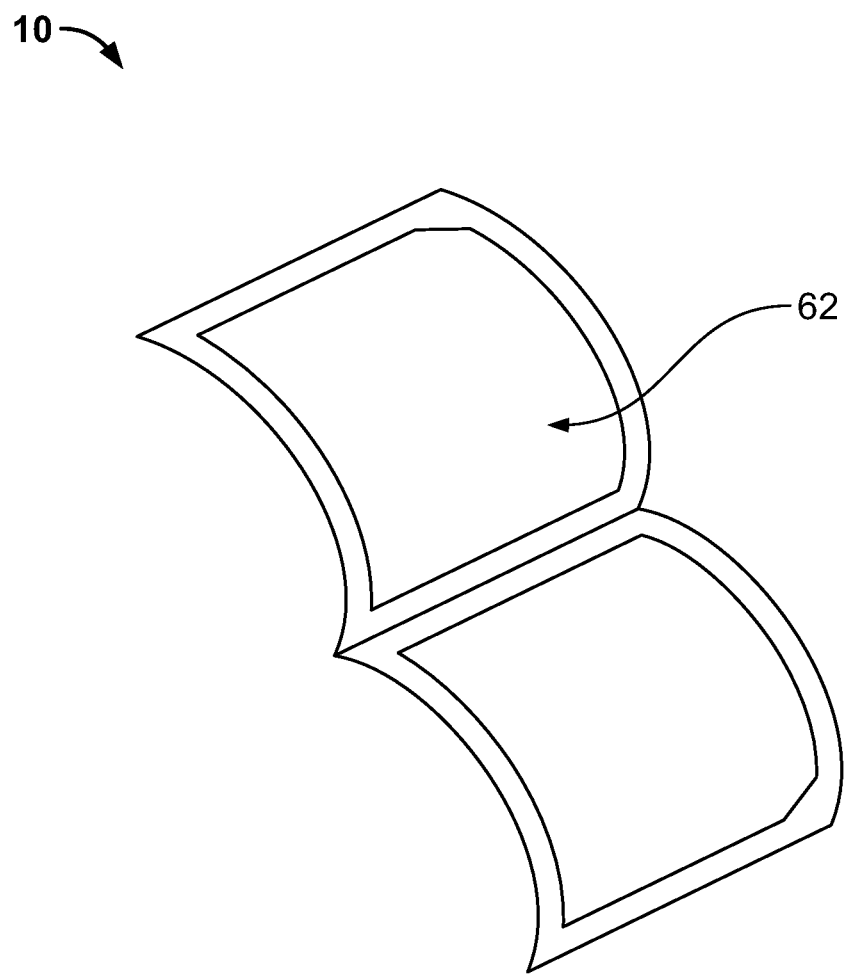
FIG. 4 is an isometric view of the dispensing device of FIG. 1 in a third state.
Figure 5:
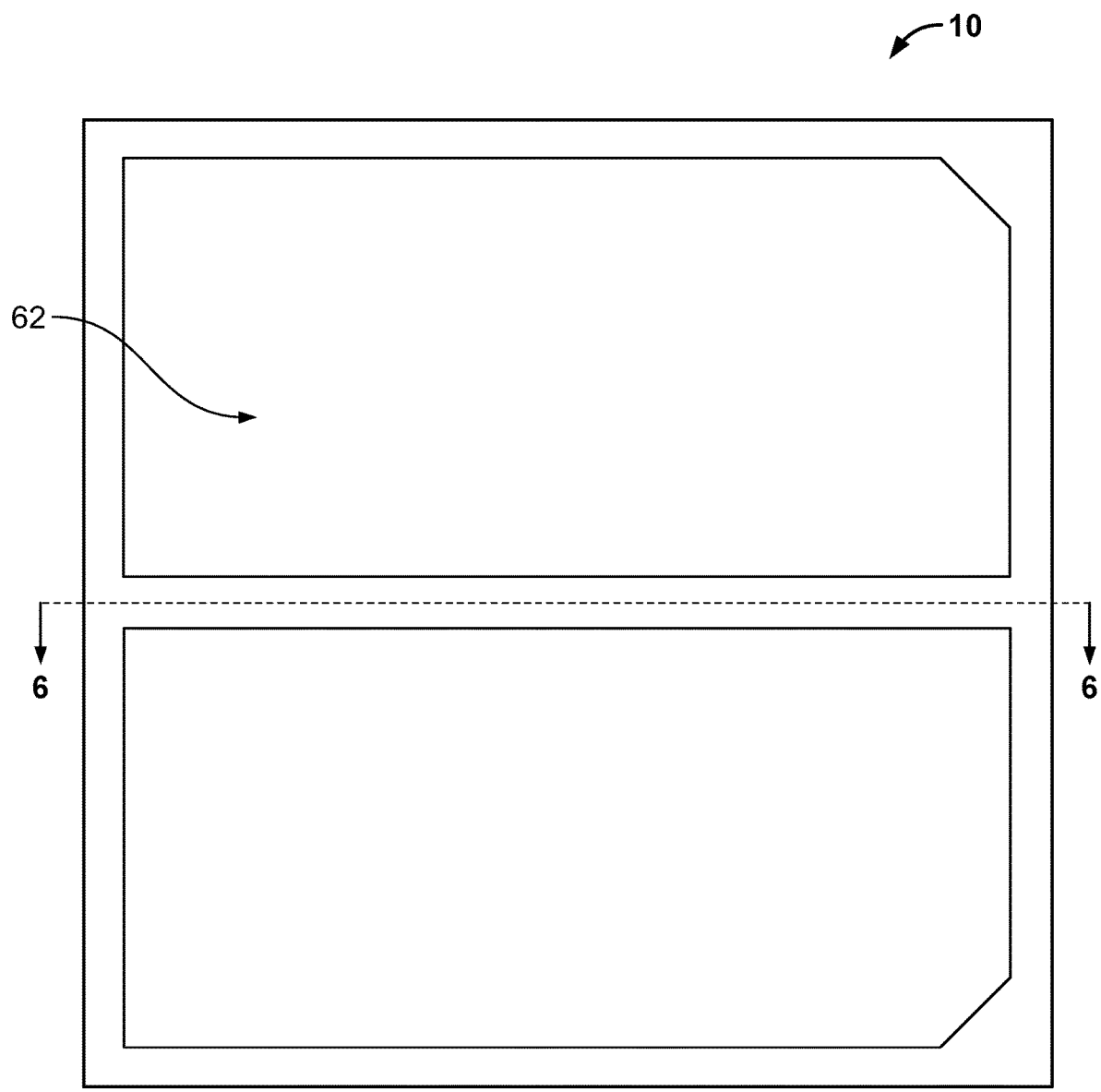
FIG. 5 is a front elevational view of the dispensing device of FIG. 4.
Figure 6:
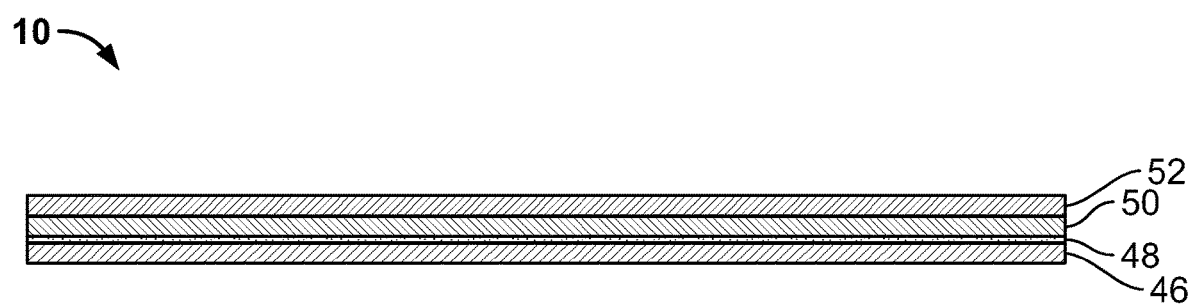
FIG. 6 is a cross-sectional view of the dispensing device of FIG. 5, taken along lines 6-6 thereof.

Other characteristics may also contribute to the selection of the material(s) for the sealant layer 52, 138. For example, the peelability, or the ability of the sealant layer 52, 138 to be easily peeled or separated from a second layer to which it is hermetically heat sealed, may contribute to the selection of the material(s) used for the sealant layer. In general, the sealant layer 52, 138 may be formed from one or more materials that provide a sufficient hermetic heat seal to retain an active agent or volatile material within the dispensing device 10, 110, while still being able to be opened using a low grip strength. As a result, the dispensing device 10, 110 may sufficiently retain the volatile material disposed therein, as well as be less likely to tear or stretch during a transition between the non-operational, or closed state, as shown in FIG. 1 and the operational, or open state, as shown in FIG. 4. Additionally, providing the dispensing device 10, 110 with a sealant layer 52, 138 that may be easily separable or opened eliminates the need of a secondary tool, e.g., a scissors, which would otherwise be required to open the dispensing device 10, 110.

In one aspect, the peel strength, or a bond strength, between a first portion of the sealant layer 52, 138 and a secondary material (e.g., a second portion of the sealant layer 52, 138) may be measured. This peel strength may measure the strength of the adhesive bond between a first portion of the sealant layer 52, 138 and a secondary material, such as a second portion of the sealant layer 52, 138 or a secondary layer, and may be defined by an average load per unit width of bond length required to part the bonded materials (i.e., the first portion of the sealant layer 52, 138 and the secondary material). An example standardized testing method that may be used to measure the average load strength, or the peel or stripping strength of an adhesive bond, is active standard ASTM D-903, provided by ASTM International.

In one aspect, the hermetic heat seal is between a first portion of the sealant layer 52, 138 and a secondary material (e.g., a second portion of the sealant layer 52, 138) and may have a peel strength, or average load strength, between about 1 Newton (N) and about 100 N, between about 1 N and about 50 N, between about 2 N and about 20 N, or between about 2 N and about 10 N.

Characteristics relevant to the stability of the sealant layer 52, 138 may also contribute to the selection of the material(s) used for the sealant layer, such as the chemical stability of the sealant layer 52, 138 when one or more active agents, solvents, or other liquids come in contact with the material(s) of the sealant layer 52, 138. For example, the material(s) of the sealant layer may be tested using a solvent resistance rub test that determines the degree of cure of the baked film by the film resistance to a specified solvent. An example standardized testing method that may be used to measure capability of a layer (such as the sealant layer 52, 138) to rub off after application of a solvent is active standard ASTM D-4752, provided by ASTM International.

Suitable materials that may be used for the sealant layer 52, 138 include one or more films constructed from an ethylene-vinyl acetate (EVA), a polyethylene, such as a low-density polyethylene (LDPE), a high molecular weight low-density polyethylene, or a linear low-density polyethylene (LLDPE), a polypropylene (PP), ethylene-butene copolymer, polybutene, butylene copolymers, an ethylene vinyl alcohol copolymer (EVOH), a polyester, a polyethylene terephthalate glycol (PETG), a polylactic acid (PLA), or a nylon. Combinations or blends (e.g., binary or ternary blends) of the aforementioned materials may also be used, which may improve the peelability of the dispensing devices 10, 110. For example, blends which may be used for the sealant layer 52, 138 are EVA-LDPE, polybutene-EVA, polybutene-LDPE-EVA, etc.

Other materials that may be suitable for use as the sealant layer 52, 138 include one or more polyethylene terephthalate film structures, such as transparent films under the trade names EZ Peel®, Mylar®, e.g., Mylar® OL, LumiLid®, e.g., Lumilid® XL 7, Lumirror®, Lumirror® XL 5, or Curlon®, all of which are either provided by DuPont, Toray Industries, Inc. or Bemis Company, Inc. In particular embodiments, the sealant layer 52, 138 may be CURLON® (Grade A9599) and W18-000832 from Bemis Company, Inc.

Adhesive Layer

An adhesive layer 48, 134 may be applied or provided on at least a portion of the inner layer 50, 136 and/or the outer layer 46, 112, or between the inner layer 50, 136 and the outer layer 46, 112, to bond, adhere or otherwise couple the inner layer 50, 136 to the outer layer 46, 112. In certain aspects, the adhesive layer 48, 134 is provided to improve the adhesion between the inner layer 50, 136 and the outer layer 46, 112 and, as result, to provide stability to the inner layer 50, 136 and the adhesive layer 52, 138 of the dispensing device 10, 110. The polymers that may be used in the adhesive layer 48, 134, or tie layer, may be an ethylene-based polymer, such as a copolymer of ethylene with a polar co-monomer or an anhydride-modified ethylene vinyl acetate polymer, a low density polyethylene, or an ethylene copolymer, or a linear low density polyethylene.

In one aspect, the adhesive layer 48, 134 may be a polymer commercially available from DuPont under trade name Bynel® and, in particular, may be a polymer having a higher amount of incorporated anhydride, such as Bynel® Series 3800 resins and, more particularly, Bynel® 3860.

Volatile Material

The dispensing device 10, 110 may include any suitable volatile material. In some embodiments, the volatile material may include an active agent, such as a fragrance, an insecticide, a deodorizer, a fungicide, a bacteriocide, a sanitizer, a pet barrier, or other active volatile or other compound disposed within a carrier liquid, e.g., an oil-based, organic based, and/or water based carrier or solvent, a deodorizing liquid, or the like, and/or combinations thereof. In particular embodiments, the dispensing device 10, 110 includes an insect control agent, an insect repellant, or an insecticide. Examples of possible insecticides that may be suitable in the volatile material include pyrethroids such as metafluthrin, transfluthrin, tefluthrin, and vaporthrin, or natural actives (geraniol, etc.) or blend of these insecticides.

Additional examples of an active agent that may be used in the volatile material may include RAID®, Pyrel®, POLIL®, AUTAN®, OUST™ or GLADE®, sold by S. C. Johnson & Son, Inc., of Racine, Wisconsin. The volatile material may also comprise other actives, such as sanitizers, air and/or fabric fresheners, cleaners, odor eliminators, mold or mildew inhibitors, insect repellents, and the like, or others that have aromatherapeutic properties. The volatile material alternatively comprises any fluid know to those skilled in the art that can be dispensed from a container, such as those suitable for dispersal in the form of particles or droplets suspended within a gas and/or propelled by means of a propellant.

In one example, a volatile material may be formed, dispensed into (e.g., with a propellant), or otherwise provided in one or more layers or reservoirs within the dispensing device 10, 110 so that when the dispensing device 10, 110 is in a closed state, the volatile material is substantially dormant, inactive, or non-volatile. However, upon opening of the dispensing device 10, 110, the volatile material may vaporize or may emanate from the dispensing device at a controlled rate of release.

In some embodiments, the active agent, such as transfluthrin, may be present in the volatile material in an amount between about 5 wt. % and about 95 wt. %, about 60 wt. % and about 90 wt. %, or between about 70 wt. % and about 85 wt. %, or even more specifically, between about 75 wt. % and about 85 wt. %. In a particular embodiment, the insect control agent may be about 80 wt. % of the volatile material and, in a preferred embodiment, transfluthrin may be about 80 wt. % of the volatile material.

The volatile material may also comprise liquids, solids, or vapors. In one aspect, the volatile material may include one or more solvents, such as an organic or aqueous solution, in which the insect control agent may be dissolved. For example, in certain aspects, the active agent may be in a solid state at room temperature, and a solvent may be added to the active agent in order to provide and keep the volatile material in a liquid state, thus allowing the volatile material to spread, be coated on, and positioned within the dispensing device 10, 110 and the one or more layers thereof, e.g., the inner layer 50, 136 and/or the sealant layer 52, 138. Further, the volatile material may be provided in a medium so that the formulation thereof spreads and coats the layers of the dispensing device 10, 110 instantaneously or within 24 hours from initial dosing.

In particular embodiments, the volatile material may contain an organic solvent, such as a hydrocarbon solvent, a glycol ether, a propylene oxide-based solvent and/or synthetic isoparaffins. For example, suitable organic solutions that may be used as a solvent for the volatile material include glycol ethers, including a dipropylene glycol n-butyl ether marketed as DOW-ANOL® DPnB solvent, Tripropylene glycol Methyl Ether marketed as DOWANOL® TPM solvent, and Dipropylene glycol Dimethyl Ether marketed as PROGLYDE™ DMM solvent, all of which are available from the Dow Chemical Company. Additional examples of solvents that may be used in the volatile material are synthetic isoparaffins under the trade name Isopar™, including but not limited to Isopar™ C, Isopar™ E, Isopar™ G, Isopar™ H, Isopar™ K, Isopar™ L, Isopar™ M, and Isopar™ V, which are available from the Exxon-Mobil Chemical Company.

A criteria for selecting the solvent is the surface tension, evaporation rate and chemical compatibility with the upper portion 40, 130. For example, the DMM surface tension (26.3 dynes) when added to transfluthrin (surface tension 44 dynes) results in a formula lower surface than the active alone, thereby allowing the active to spread on the multi-layer surface and ensure coverage across the surface area of the dispensing device 10, 110. Another role for the solvent is to reduce the viscosity of the active agent for ease of processing, and chemical compatibility with the adhesive and other components of the dispensing device 10, 110.

Even further, it was also discovered that glycol ethers, e.g. DMM, suppress the recrystallization of the actives that are solid at room temperature, e.g., Transfluthrin (TFT). And this suppression of crystallization keeps the active in a solution and improves the aesthetics of the dispensing device 10, 110.

The volatile material may include a solvent, which may be present in the volatile material in an amount between 10 wt. % and about 30 wt. %, or between about 15 wt. % and about 25 wt. %, and in a particular embodiment, 20 wt. %. In one aspect, the volatile material includes about 20 wt. % of di-propylene glycol dimethyl ether.

As discussed herein, in certain aspects, the volatile material may be stabilized within the dispensing device 10, 110 when the dispensing device 10, 110 is in a closed, non-operative state, such as that shown in FIG. 1. For example, in some embodiments, the dispensing device 10, 110 can retain an initial dosage applied to the dispensing device 10, 110 for a fixed time, such as six hours, twelve hours, one day, two days, three days, four days, five days, six days, one week, ten days, two weeks, fifteen days, twenty days, three weeks, twenty-five days, four weeks, thirty days, five weeks, forty days, six weeks, forty-five days, seven weeks, fifty days, fifty-five days, eight weeks, and the like. In some embodiments, when in a closed, non-operative and sealed state, the dispensing device 10, 110 may retain at least about 70% of the volatile material disposed therein, for example. In preferred embodiments, when in a closed, non-operative, and sealed state, the dispensing device 10, 110 may retain at least about 85% of the volatile material disposed therein, at least about 90% of the volatile material disposed therein, at least about 95% of the volatile material disposed therein, or at least about 98% of the volatile material disposed therein over a fixed time. In these preferred embodiments, the fixed time may be about 2 weeks, about 4 weeks, about 12 weeks, or a fixed time greater than 12 weeks.

In other aspects, the dispensing device 10, 110 can provide delivery of the volatile material from the dispensing device 10, 110 at an initial delivery rate that is measured within one hour of exposing the volatile material and the dispensing device 10, 110 to the atmosphere. The dispensing device 10, 110 can provide delivery of the volatile material across, or from, the inner layer 50, 136 at a subsequent delivery rate that is measured at a fixed time after exposing the volatile material and the interior 62 of the dispensing device to the atmosphere. The fixed time can be any length of time over which the vapor-dispensing device is desired to provide delivery of the volatile composition. For example, the fixed time can be six hours, twelve hours, one day, two days, three days, four days, five days, six days, one week, ten days, two weeks, fifteen days, twenty days, three weeks, twenty-five days, four weeks, thirty days, five weeks, forty days, six weeks, forty-five days, seven weeks, fifty days, fifty-five days, eight weeks, and the like.

In certain aspects, the particular surface area and formulation concentration of the dispensing device 10, 110 may be designed to emanate between about 0.1 mg/day and about 10 mg/day of the active agent or the volatile material, between about 1 mg/day and about 5 mg/day of the active agent or the volatile material, or between about 1.5 mg/day and about 4 mg/day or the active agent or the volatile material. Likewise, the dosage of the embodiment at fixed surface area is selected based on the desired duration from weeks, months or seasons. For example, if the dispensing device 10, 110 is designed to have an emanation rate of about 2 mg active agent/day then a dispensing device 10, 110 designed for use for one month will be dosed with at least 60 mg of an active agent (e.g., transfluthrin). As another example, if the dispensing device 10, 110 is designed to have an emanation rate of about 2 mg active agent/day, then a dispensing device 10, 110 designed for use for three months (i.e., for a season) will be dosed with at least 160 mg of an active agent (e.g., transfluthrin). Hence, initial dosage level of the volatile material and/or the active agent therein may vary from 1 mg to 5 g depending on desired surface area, desired emanation rate, and/or desired emanation lifetime.

As discussed above, in some embodiments, the dispensing device 10, 110 may be initially dosed with the volatile material and/or the active agent with a predetermined initial dosage. In particular aspects, the initial dosage of the volatile material and/or the active agent therein may range between about 1 mg and about 5 g, between about 20 mg and about 2 g, between about 20 mg and about 1 g, between about 20 mg and about 200 mg, between about 40 mg and about 100 mg, or between about 55 mg and about 70 mg. In one example, a dispensing device 10, 110 may be initially dosed with about 68.75 mg of volatile material, which may comprise approximately 55 mg of an active agent (e.g., transfluthrin or methofluthrin) and approximately 13.75 mg of a solvent (e.g., a di-propylene glycol dimethyl ether). In another example, a dispensing device 10, 110 may be initially dosed with about 137.5 mg of volatile material that may comprise approximately 110 mg of an active agent (e.g., transfluthrin or methofluthrin) and approximately 27.5 mg of a solvent (e.g., a di-propylene glycol dimethyl ether).

Although amounts of an initial dosage are outlined above with regard to particular embodiments, it should be understood by one skilled in the art that the initial dosage may vary and may be dependent on a combination of factors, including but not limited to, the surface area of the interior 62 of the dispensing device 10, 110 to which the volatile material is applied, the thickness of the one or more layers to which the volatile material may be applied (e.g., a thickness of the inner layer 50, 136 or a thickness of a sealant layer 52, 138, individually or in combination), a desired delivery rate of the volatile material from the dispensing device 10, 110, a type of material(s) used for the one or more layers of the dispensing device 10, 110 (e.g., a type of material(s) used for the inner layer 50, 136, a type of material(s) used for the sealant layer 52, 138, a type of material(s) used for the outer layer 46, 112, or a type of material(s) used for the sealant layer 48, 134), or a type of volatile material(s) used in the dispensing device 10, 110.

Figure 15:
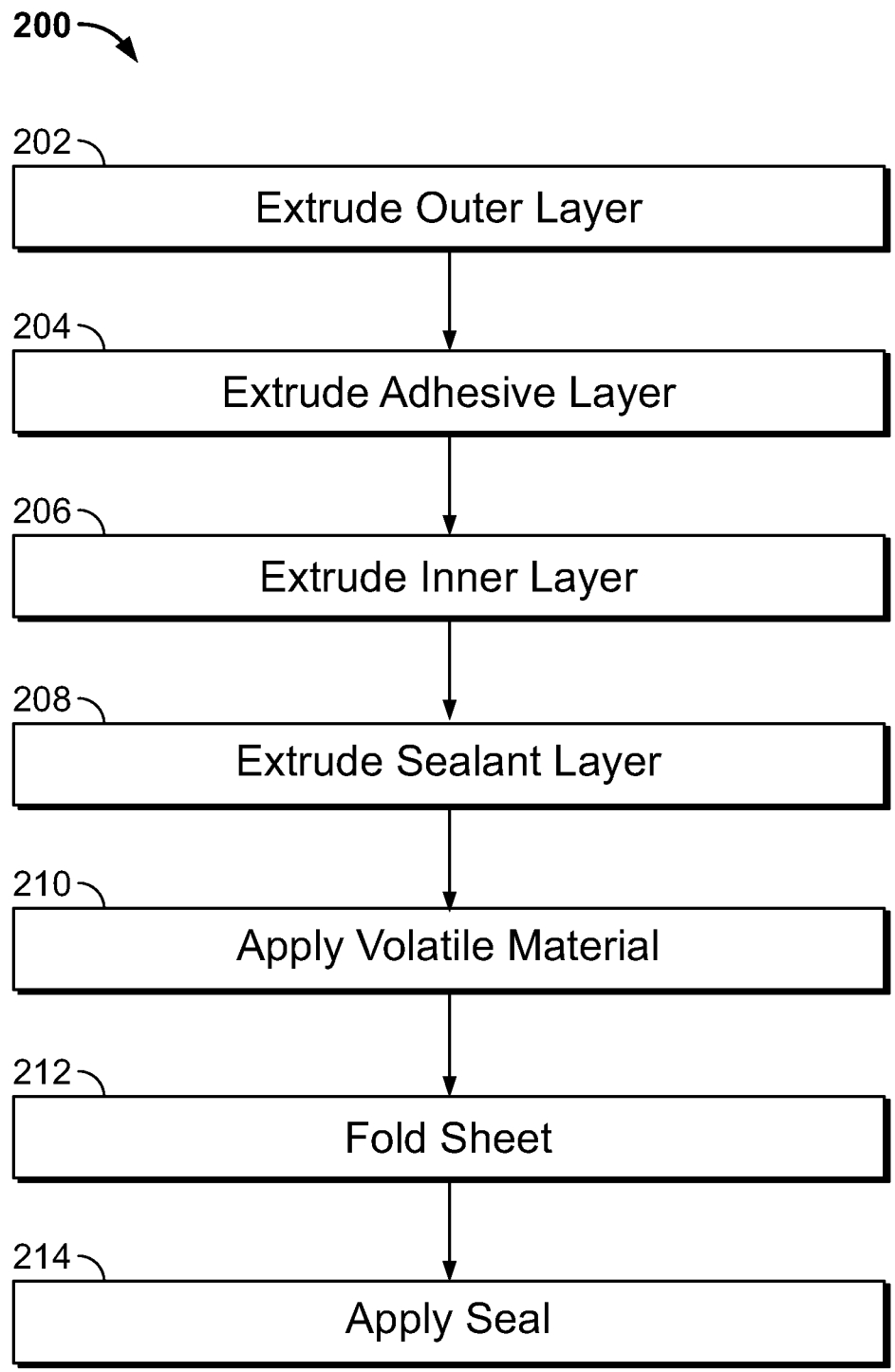
FIG. 15 is a flow chart for an example methodology used to make the dispensing device of FIGS. 1-8 or the dispensing device of FIGS. 9-14.

FIG. 15 depicts an illustrative method 200 for making the dispensing device 10 or the dispensing device 110. In general, the process 200 may be schematically illustrated with steps 202, 204, 206, 208, 210, 212, and 214. First, in step 202, the one or more materials of the outer layer 46, 132 of the dispensing device 10, 110 may be extruded. Next, in step 204, the one or more materials of the sealant layer 48, 134 maybe extruded on top of the outer layer 46, 132, and in step 206, the one or more materials of the inner layer 50, 136 may be extruded on top of the sealant layer 48, 134. Further, in the next step 208, the sealant layer 52, 138 may be extruded onto the inner layer 50, 136 and the extruded layers of the dispensing device 10, 110 may be cooled or allowed to sit for a predetermined amount of time. After the layers of the dispensing device 10, 110 are formed, an initial dosage of the volatile material may be applied to the inner layer 50, 136 and/or the sealant layer 52, 138 of the dispensing device 10, 110 at step 210.

In certain embodiments, the dispensing device may then be folded at step 212. In particular, the dispensing device 10, 110 may be folded upon itself so that a top or upper layer 40 of the dispensing device 10, 110 is positioned over a bottom or lower portion 42. After the dispensing device 10, 110 is folded, an application of a moderate amount of heat, for example, by way of a platen press, may be applied to an outer layer 46, 132 of the dispensing device 10, 110. Preferably, heat in the range of 90 degrees Celsius to about 320 degrees Celsius may be applied to the outer layer 46, 132 for a predetermined amount of time, and pressure thereby forming a hermetic heat seal between the upper layer 40 and the lower portion 42 of the dispensing device 10, 110 and, in particular, a hermetic heat seal between a first portion of the sealant layer 52, 138 and a second portion of the sealant layer 52, 138.

Figure 16:
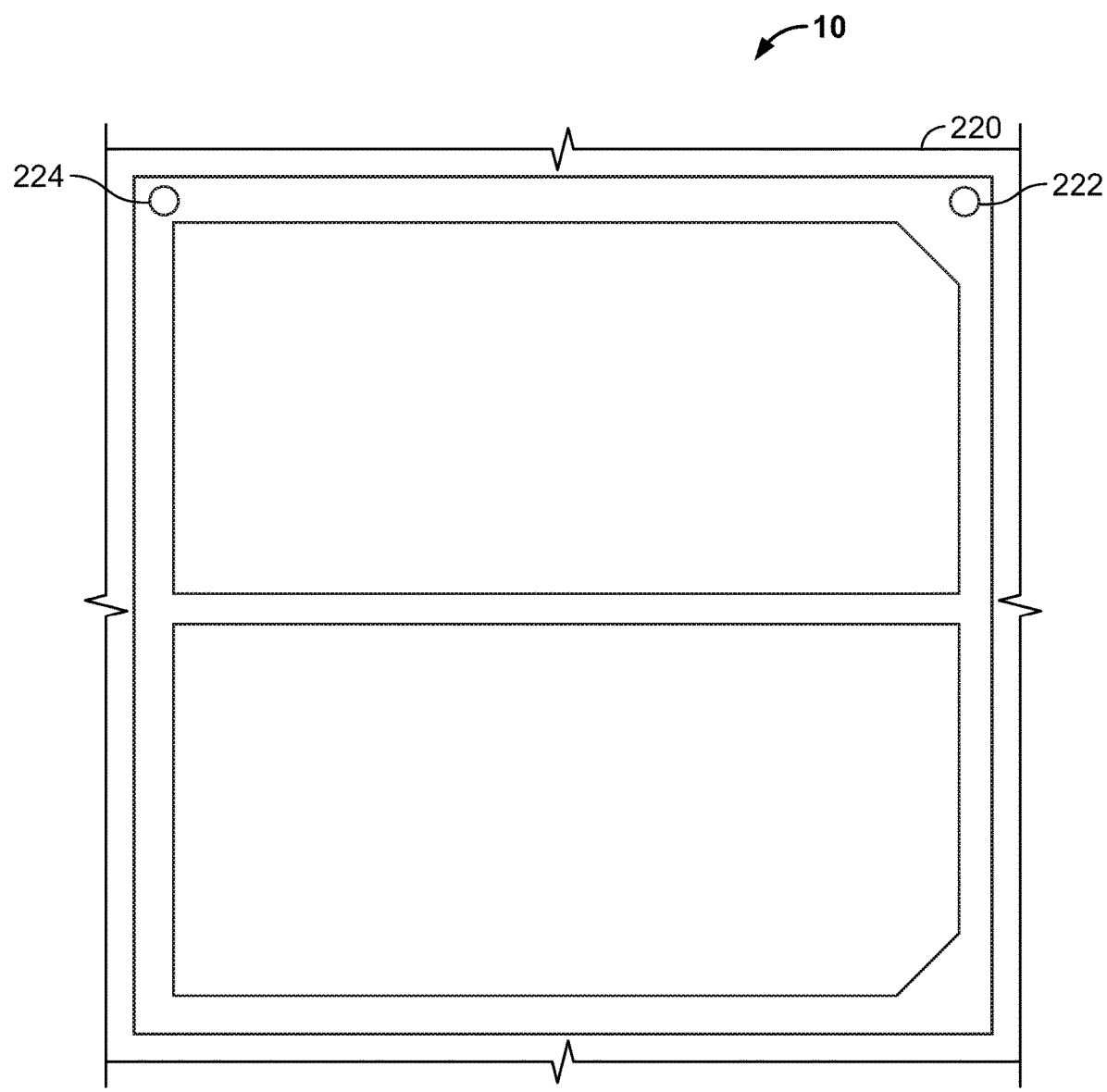
FIG. 16 is a front elevational view of a dispensing device mounted to a surface.
Figure 17:
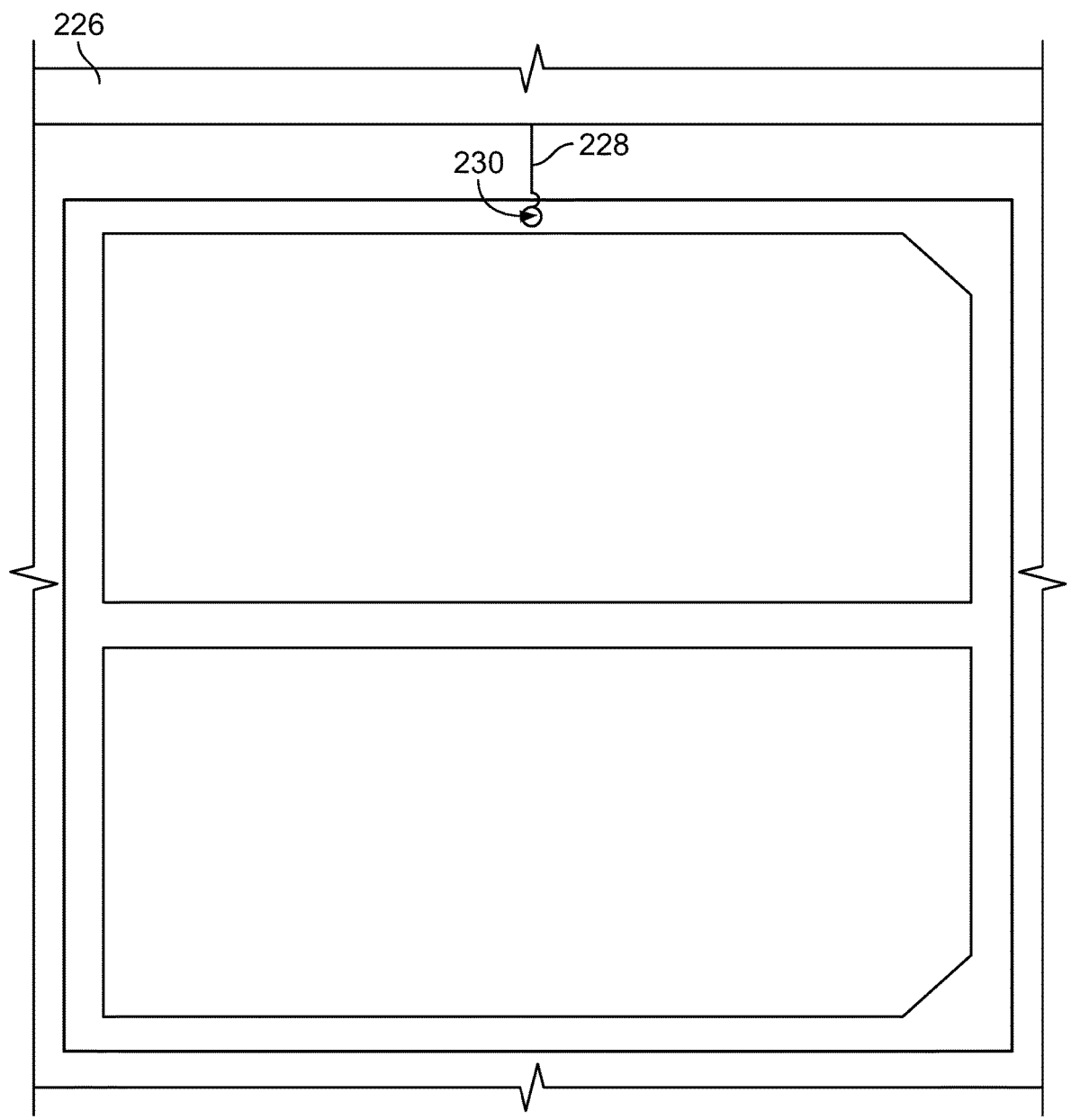
FIG. 17 is a front elevational view of a dispensing device hung from a surface.
Figure 18:
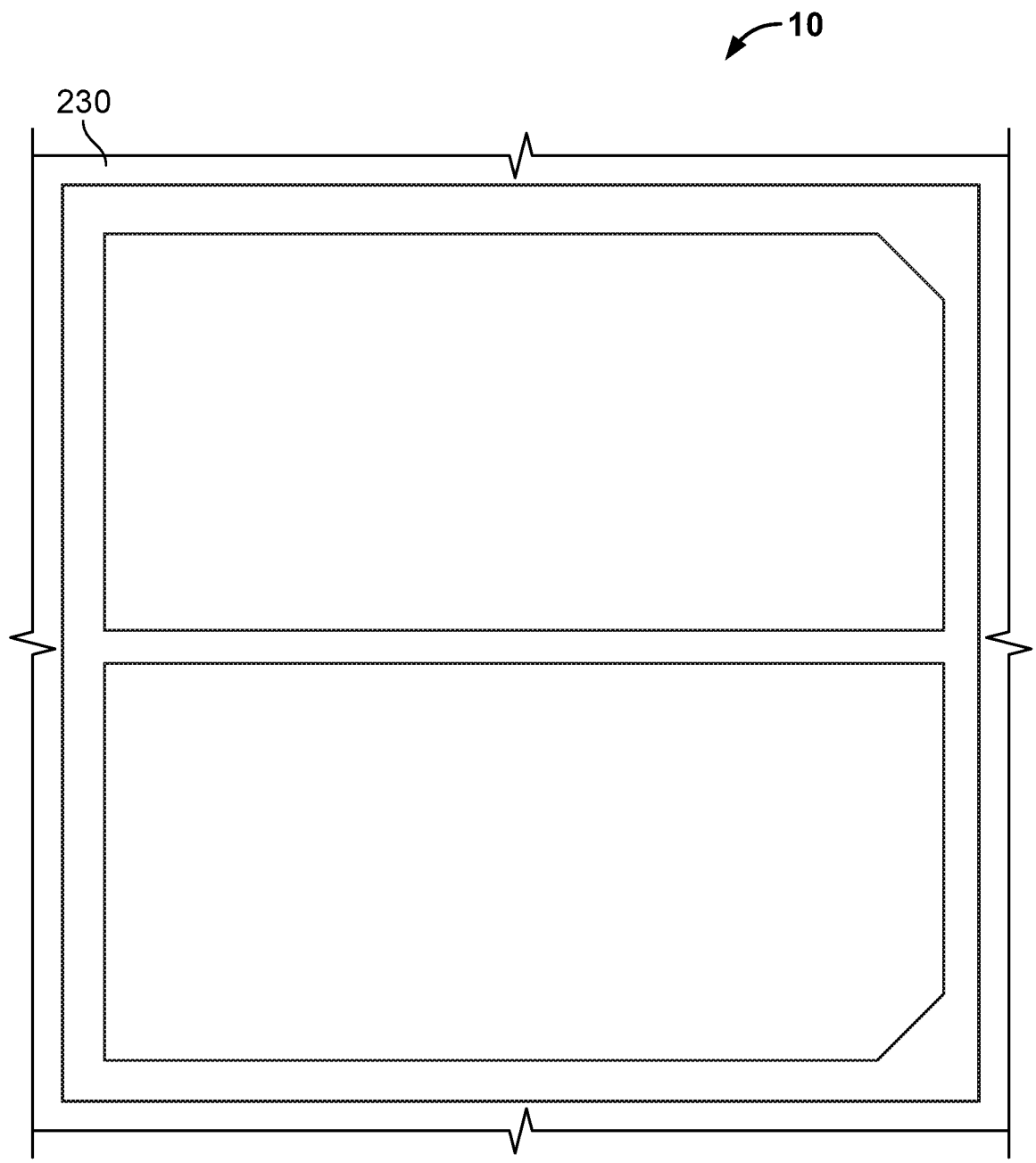
FIG. 18 is a front elevational view of a dispensing device mounted to a surface.

As discussed herein, the outer layer 46, 132 of the dispensing device 10, 110 may be formed using one or more materials that possess good thermal properties and provide sufficient support and strength to the dispensing device 10, 110. In this regard, the outer layer 46, 132 may provide the dispensing device 10, 110 with a high-tensile strength that prevents the dispensing device 10, 110 from curling or ripping during operational use. For example, as shown in FIG. 16, the dispensing device 10, or alternatively the dispensing device 110, may be adhered to a surface 220 using two points of contact 222, 224. In an alternative embodiment, the dispensing device 10, or alternatively the dispensing device 110, may be hung from a surface 226 using a hook or string 228 positioned through an aperture 230, as shown in FIG. 17. Still further, as shown in FIG. 18, the dispensing device 10, 110 according to the aspect depicted in FIGS. 7, 8, and 14, may be adhered to a surface 230 using the mounting element 64, 144.

EXAMPLES

The examples herein are intended to illustrate certain embodiments of the dispensing device 10, 110 to one of ordinary skill in the art and should not be interpreted as limiting in the scope of the disclosure set forth in the claims. The dispensing device 10, 110 may comprise the following non-limiting examples.

Example 1

As discussed herein, characteristics relevant to the peelability and/or stability of the sealant layer 52, 138 may contribute to the selection of the material(s) used for the sealant layer 52, 138, such as the capability of the sealant layer 52, 138 to be easily peeled open or separated from a second layer to which the sealant layer 52, 138 is hermetically heat sealed to, or the capability of the sealant layer 52, 138 to rub off after application of a solvent thereto.

A number of materials were selected to be tested for the sealant layer 52, 138 and subsequently tested on their ability to form a hermetic heat seal and their ability to be subsequently peeled apart, as well as their ability to not rub off after coming into contact with a solvent. In particular, 14 different materials were first tested based on their peelability and each material was generally classified as either easy to peel or unpeelable. Next, the same materials were tested based on their chemical stability (or cure). In this testing, a di-propylene glycol dimethyl ether was applied to each material and each material was generally classified based on the ability of the sealant to rub off of the material. The data collected is shown in Table 1.

TABLE 1

Evaluation of Sealant Layers

| Material | Sealability & Peelability | DMM Solvent Rub Test |
|---|---|---|
| DuPont Mylar ® OL (Biaxially oriented polyester (OPET) film with an amorphous polyester heat seal layer) | Easy Peel | Sealant Rubbed Easily |
| DuPont Mylar ® OL12 (Biaxially oriented polyester film (OPET) with an amorphous polyester heat seal layer) | Unpeelable | Sealant Rubbed Easily |
| DuPont Mylar ® OWF (Co-extruded, one side amorphous, heat sealable polyester film) | Unpeelable | Did Not Rub Off |
| Roll Print 26-1267 (Laminated composite of polyester, white polyethylene, aluminum foil, and polyester sealant) | Easy Peel | Did Not Rub Off |
| Roll Print 26-1268 (Laminated composite of polyester, white polyethylene, aluminum foil, and polyester coex sealant) | Easy Peel | Did Not Rub Off |
| Roll Print 26-1269 (Laminated composite of polyester, white polyethylene, aluminum foil, and coex sealant) | Easy Peel | Did Not Rub Off |
| Roll Print 26-1271 (Oriented polyester film with polyester sealant) | Easy Peel | Did Not Rub Off |
| Toray Plastics LumiLid ® XL 7 (PET/PP Sealant) | Unpeelable | Did Not Rub Off |
| Toray Plastics LumiLid ® XL 5 (PET/Sealant) | Unpeelable | Did Not Rub Off |
| Toray XP 089 - 04B60728 (PET based film with a Olefin based high performance sealant layer) | Easy Peel | Did Not Rub Off |
| Toray XP 089 - 03B60728 (PET based film with a Olefin based high performance sealant layer) | Easy Peel | Did Not Rub Off |
| Toray XP 735 (PET based film with a Olefin based high performance sealant layer) | Unpeelable | Did Not Rub Off |
| Toray XP 781 (PET based film with a Olefin based high performance sealant layer) | Unpeelable | Did No Rub Off |
| Bemis Lidding Film | Easy Peel | Did Not Rub Off |

Example 2

Figure 21:
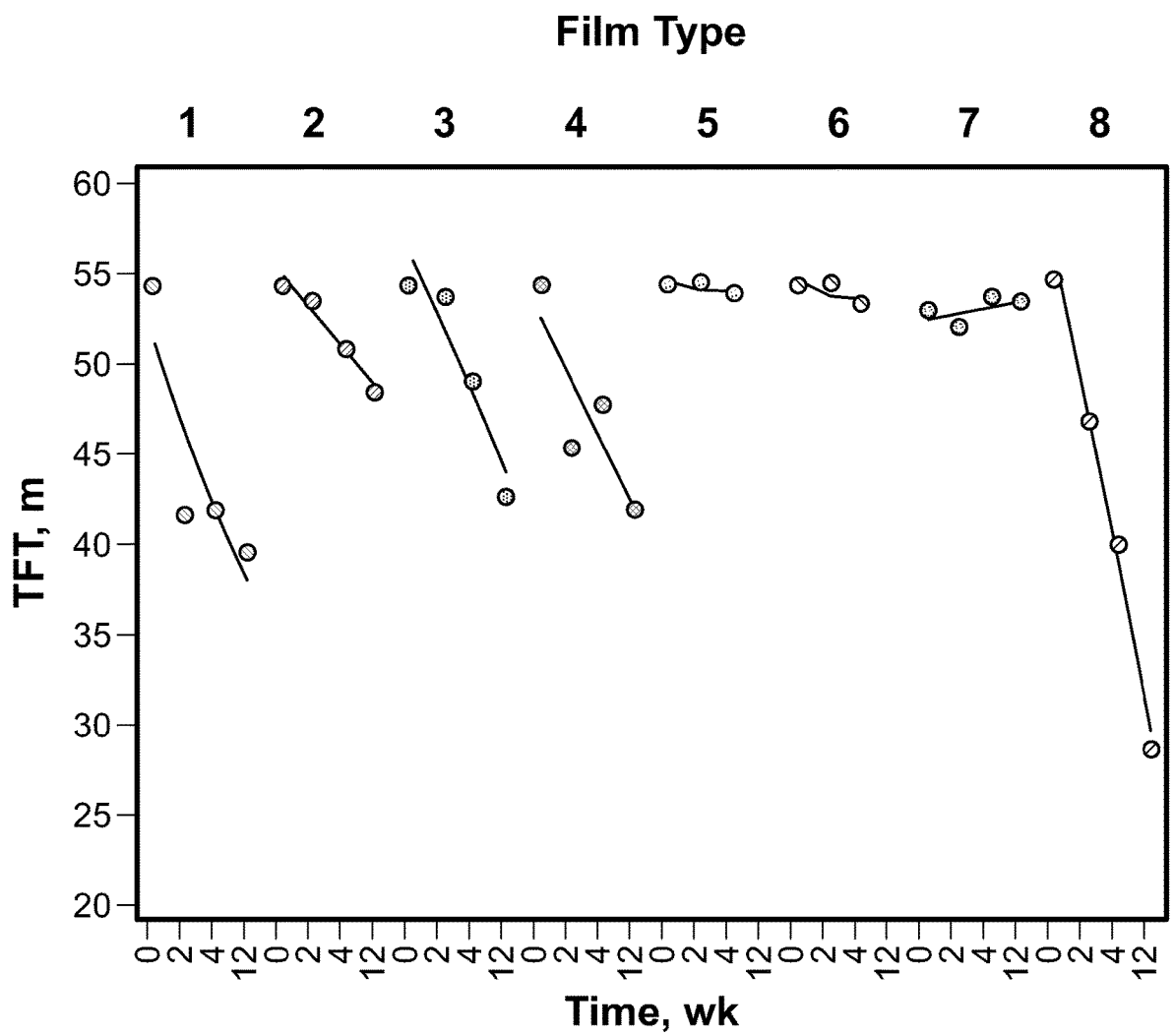
FIG. 21 is a graph illustrating the stability of a volatile material within a plurality of dispensing devices having a variety of films at a loading level of 55 mg of an active agent.

A number of the materials from Example 1 were subsequently tested based on their ability to retain a volatile material therein. In particular, for each material, a dispensing device was constructed and dosed with an initial concentration of 68.75 mg of the volatile material, including about 80 wt. % transfluthrin (approximately 55 mg) and about 20 wt. % PROGLYDE™ di-propylene glycol dimethyl ether (approximately 13.75 mg), and subsequently sealed. Each dispensing device was stored in high temperature conditions, i.e., in an environment having a constant temperature of about 54 degrees Celsius, and the concentration of volatile material at 2 weeks, 4 weeks, and 12 weeks were measured. The data collected is illustrated in FIG. 21 and, in addition, Table 2 details what films from Example 1 were tested and plotted in FIG. 21.

TABLE 2

| Film Type | Solubility Material |
|---|---|
| 1 | 26-1267 |
| 2 | 26-1268 |
| 3 | 26-1269 |
| 4 | 26-1271 |
| 5 | Toray XP 089 - 03B60728 (72G-03) |
| 6 | Toray XP 089 - 04B60728 (72G-04) |
| 7 | Bemis |
| 8 | MSP* |

*Not in Example 1

Data collected for the eight different materials, which may be used for the sealant layer 52, 138, exhibited either complete retention of the volatile material or a loss of volatile material in each respective dispensing device. Based on the data, it was determined that an amount of volatile material may be completely, or almost completely, retained by a dispensing device that utilizes a polyester film provided by Toray Plastics, Inc. (i.e., film types 5 and 6 in FIG. 21 and Table 2), or a nylon based multilayer film by Bemis Company, Inc. (i.e., film type 7 in FIG. 21 and Table 2).

It was also determined that the decrease in the active agent or volatile material within the dispensing device 10, 110 over time was either due to the permeation of the active agent or volatile material through the film or leaching of the active agent or volatile material through the hermetic seal between the sealant layer 52, 138.

As noted herein, typically, materials capable of retaining an active agent or a volatile material, such as a transfluthrin used in the Examples herein, are incapable of forming a hermetic heat seal, or vice-versa, materials capable of forming sufficient hermetic seals are not expected to adequately store or retain a volatile material. However, as shown in Examples 1-3, the unexpected and surprising discovery was made that some materials capable of retaining volatile materials (e.g., transfluthrin or metofluthrin) may also form adequate hermetic heat seals that sufficiently retain the volatile materials therein.

Example 3

Additionally, as discussed herein, it was surprisingly determined that a combination or selection of the inner layer 50, 136 and the sealant layer 52, 138 may provide a sealed dispensing device 10, 110 with the capability of containing a high dosage of an active agent or a volatile material in a stable environment, i.e., an environment that retains substantially all of an initial dosage of the active agent or volatile material in the dispensing device 10, 110 for a prolonged period of time (e.g., two to twelve weeks, and above), within the dispensing device 10.

For example, in one aspect, the inner layer 50, 136 includes at least one material that is adapted to dissolve, or partially dissolve, the active agent or the volatile material that is used. Further, in some embodiments, one or more layers of the sealant layer 52, 138 individually or in combination, may be adapted to be permeable or non-permeable to the volatile material or active agent within the dispensing device. In order to determine the capability of the material(s) of the inner layer 50, 136, or alternatively the sealant layer 52, 138, to dissolve and retain an active agent or a volatile material, Hansen solubility parameters and Relative Energy Difference (RED) values may be assessed.

For instance, in one embodiment, a number of materials were selected for the inner layer 50, 136 (or sealant layer 52, 138). For each material, a Relative Energy Difference (RED) value was calculated using parameters for the respective material and their respective Hansen parameters in connection with transfluthrin, which was used as an exemplary active agent for a volatile material. More particularly, 58 different materials were tested based on their capability to dissolve transfluthrin therein. In this testing, Hansen parameters were determined for the 58 different polymers and Hansen parameters were determined for transfluthrin, and RED values were calculated using Equations 1 and 2 described herein. The calculated RED values are shown in Table 3 below.

TABLE 3

Evaluation of Inner and Sealant Layer

| Material | RED Value for Polymer (with Transfluthrin pair at room temperature) |
|---|---|
| Polyvinylidene fluoride (PVDF) | 1.29 |
| Polyvinylidene fluoride (PVDF) | 2.53 |
| Silicone example | 2.08 |
| Baysilon UD 125 (silicone resin) | 2.05 |
| Silicone | 0.56 |
| Polysulfone (PSU) | 1.80 |
| Polysulfone (PSU) | 1.29 |
| Acrylonitrile butadiene styrene (ABS) | 1.15 |
| Styrene/acrylonitrile copolymer (30% AN) | 1.78 |
| Styrene/acrylonitrile copolymer (30% AN) | 1.50 |
| Nylon 11 | 1.90 |
| Polyethylene (PE) | 1.54 |
| Polyethylene (PE) | 1.57 |
| Nylon 6 | 1.97 |
| Polyphenyleneoxide (PPO) CR | 1.35 |
| Polyphenyleneoxide (PPO) | 1.45 |
| Polybutylene terephthalate | 2.47 |
| Polyvinylchloride (PVC) | 1.61 |
| Vipla KR (PVC) | 3.94 |
| Polyvinylchloride (PVC) | 1.06 |
| Mylar PET | 2.25 |
| PET mylar/R PET | 2.76 |
| Polycarbonate (PC) | 1.45 |
| Polycarbonate (PC) | 1.42 |
| Polysar 5630 (SBR) | 1.87 |
| R SBR | 1.04 |
| Nylon 6,6 | 1.49 |
| Nylon 6,6 | 2.88 |
| Polyethylene terephthalate glycol (PETG) | 2.10 |
| Lucite 2044 PMMA | 0.87 |
| Polymethyl methacrylate (PMMA) | 1.48 |
| PMMA CR (Chemical Resistance) | 0.63 |
| PMMA | 1.05 |
| Polyvinylalcohol (PVOH) | 1.82 |
| Polyvinylalcohol (PVOH) | 1.43 |
| Polyvinylalcohol (PVOH) | 0.99 |
| Polystyrene LG | 1.58 |
| Polystyrene (PS) | 1.17 |
| Polystyrene (PS) | 1.69 |
| Polypropylene (PP) | 1.89 |
| Polypropylene (PP) | 2.16 |
| Polyethylene terephthalate (PET) | 1.45 |
| Polyethylene terephthalate (PET) | 1.93 |
| Polyethether Imide (PEI) | 3.18 |
| Polyethether Imide (PEI) | 2.22 |
| PEN (Polyethylenenaphthlene) | 3.39 |
| Poly(ethylene-co-vinyl acetate) (EVA) 4055 | 2.56 |
| Sol | |
| PES Sol | 2.36 |
| Polyethersulfone (PES) | 1.87 |
| Barex 210 CR | 1.46 |
| Barex 210 CR-Styrene | 1.69 |
| High density polyethylene (HDPE) | 7.34 |

TABLE 3-continued

Evaluation of Inner and Sealant Layer

| Material | RED Value for Polymer (with Transfluthrin pair at room temperature) |
|---|---|
| Ethylene Vinyl Alcohol EVOH Sol | 2.30 |
| Polyoxymethylene (polyacetal) (POM) | 1.82 |
| Polyoxymethylene | 1.21 |
| Polyethylene oxide (PEO, PEG) | 1.25 |
| Polyacrylonitrile (PAN) | 1.80 |
| Polyacrylonitrile (PAN) | 2.62 |

Based on the Relative Energy Difference values calculated, preferred materials that may be used for the inner layer 50, 136 or sealant layer 52, 138 were determined. For example, materials exhibiting an RED value between about 0.5 and 15, or between about 0.5 and about 10, or between about 0.5 and 8 may be preferable materials for the inner layer 50, 136 when transfluthrin is used as an active ingredient in the volatile material. In other embodiments, materials exhibiting an RED value greater than 1, greater than 2, or greater than 5 may be preferable materials for the inner layer 50, 136 when transfluthrin is used as an active ingredient in the volatile material.

In addition, it was surprisingly determined that of the materials listed in Table 3, a polyester film, a polyvinyl alcohol film, a polypropylene film, an ethylene-vinyl acetate film, a high-density polyethylene film, or an ethylene vinyl alcohol film create adequate hermetic heat seals, as discussed herein. As such, the aforementioned materials are capable of both retaining an active agent or volatile material and forming a hermetic seal to retain the active agent or volatile material therein.

Example 4

Figure 22:
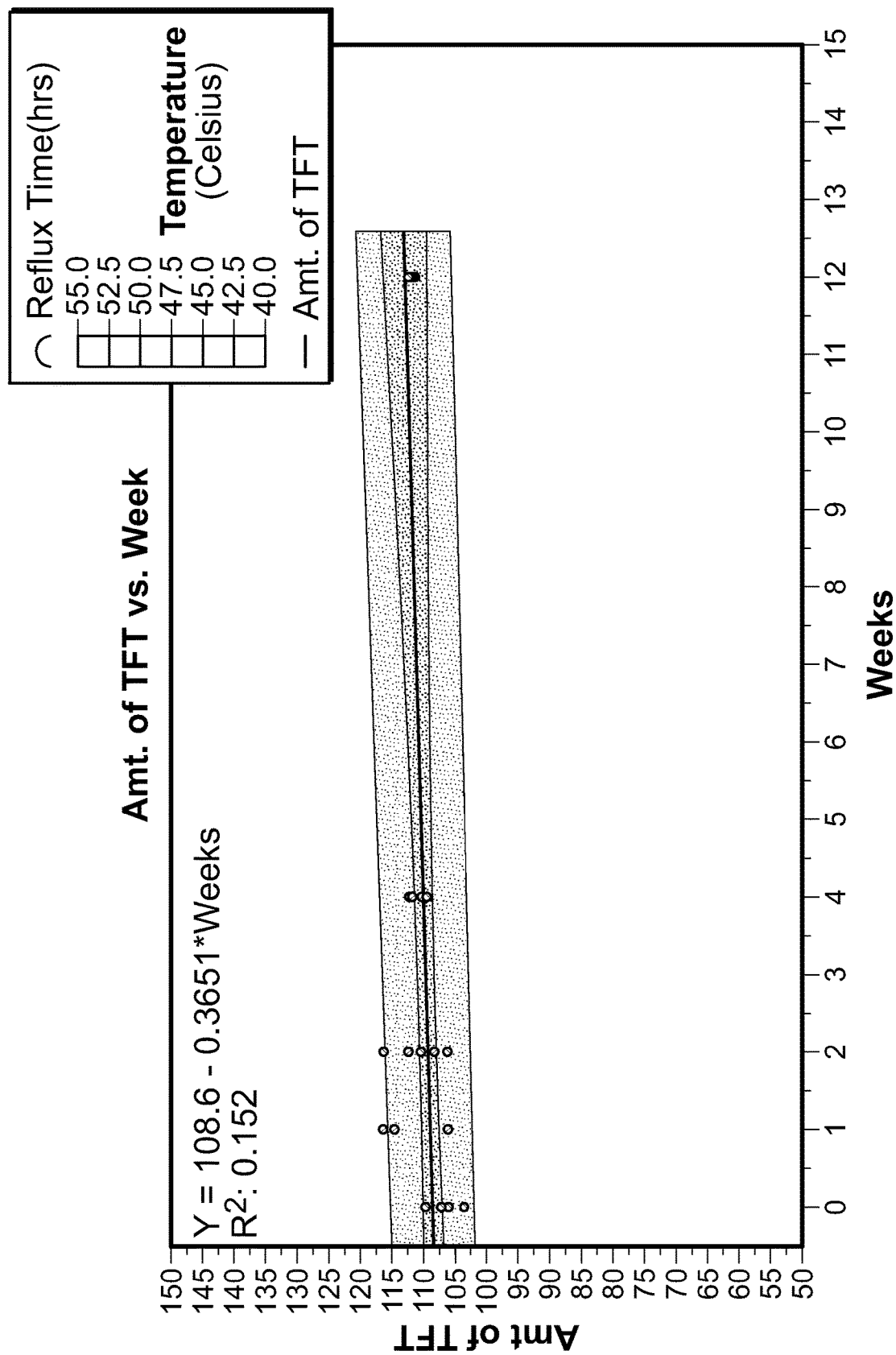
FIG. 22 is another graph illustrating the stability of a volatile material within a dispensing device having a loading level of 110 mg of an active agent.

Multiple dispensing devices incorporating a high-density polyethylene as the outer layer 46, 132, a nylon-based material as the inner layer 50, 136, and an ethylene vinyl alcohol as the sealant layer 52, 138 were constructed. The dispensing devices were then dosed with approximately 137.5 mg of volatile material, including 110 mg of transfluthrin as an active agent, and hermetically heat sealed. Next, the dispensing devices were subjected to temperatures ranging anywhere between 40 degrees Celsius and 55 degrees Celsius for a fixed amount of time ranging between about 0 weeks to about 12 weeks. In particular, the level or concentration of the transfluthrin remaining within the dispensing devices were measured after 1 week, after 2 weeks, after 4 weeks, and after 12 weeks. The data was resultantly plotted and the data is shown in FIG. 22.

As discussed herein, it was surprisingly determined that an optimal combination or selection of the outer layer 46, 132, the inner layer 50, 136, the sealant layer 52, 138, and/or the volatile material for the dispensing device 10, 110 may provide a dispensing device capable of containing a high dosage of an active agent or a volatile material (such as a dosage of 137.5 mg) within the dispensing device 10, 110 in a stable environment, i.e., an environment that retains substantially all of an initial dosage of the active agent or volatile material in the sealed dispensing device 10, 110 for a prolonged period of time (e.g., two to twelve weeks, and above). Further, based on this experimentation and the data depicted in FIG. 22, it was determined that a preferred embodiment of the dispensing device 10, 110 includes an outer layer 46, 132 having a high-density polyethylene, an inner layer 50, 136 having a nylon-based material, a sealant layer 52, 138 having an ethylene vinyl acetate, and a volatile material containing transfluthrin as an active agent therein. Even further, based on the data shown in FIG. 22, it was determined that such a dispensing device may retain at least about 90% of the initial dosage of a volatile material containing transfluthrin as the active agent.

Figure 23:
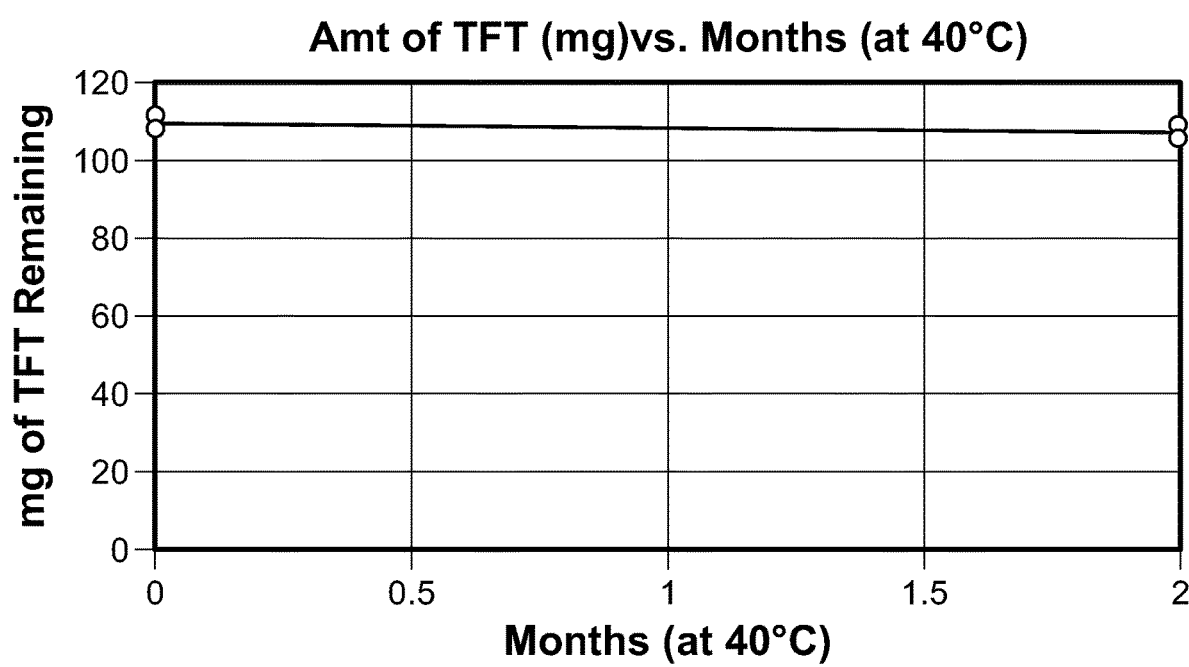
FIG. 23 is yet another graph illustrating the stability of a volatile material within a dispensing device at a loading level of 110 mg of an active agent.

Further dispensing devices similar to the dispensing device discussed above were dosed with approximately 137.5 mg of volatile material, including 110 mg of transfluthrin as an active agent, and hermetically heat sealed. Next, the dispensing devices were subjected to temperatures around 40 degrees Celsius for a fixed amount of time ranging between about 0 months to 2 months. In particular, the level or concentration of the transfluthrin remaining within the dispensing devices were measured after 2 months for multiple dispensing devices, and the data was resultantly plotted and the data is shown in FIG. 23. As shown in FIGS. 22 and 23, the dispensing devices retained at least about 85%, at least about 90%, at least about 95%, and at least about 98% of the initial dosage after prolonged periods of time (e.g., after 12 weeks or 2 months).

Figure 24:
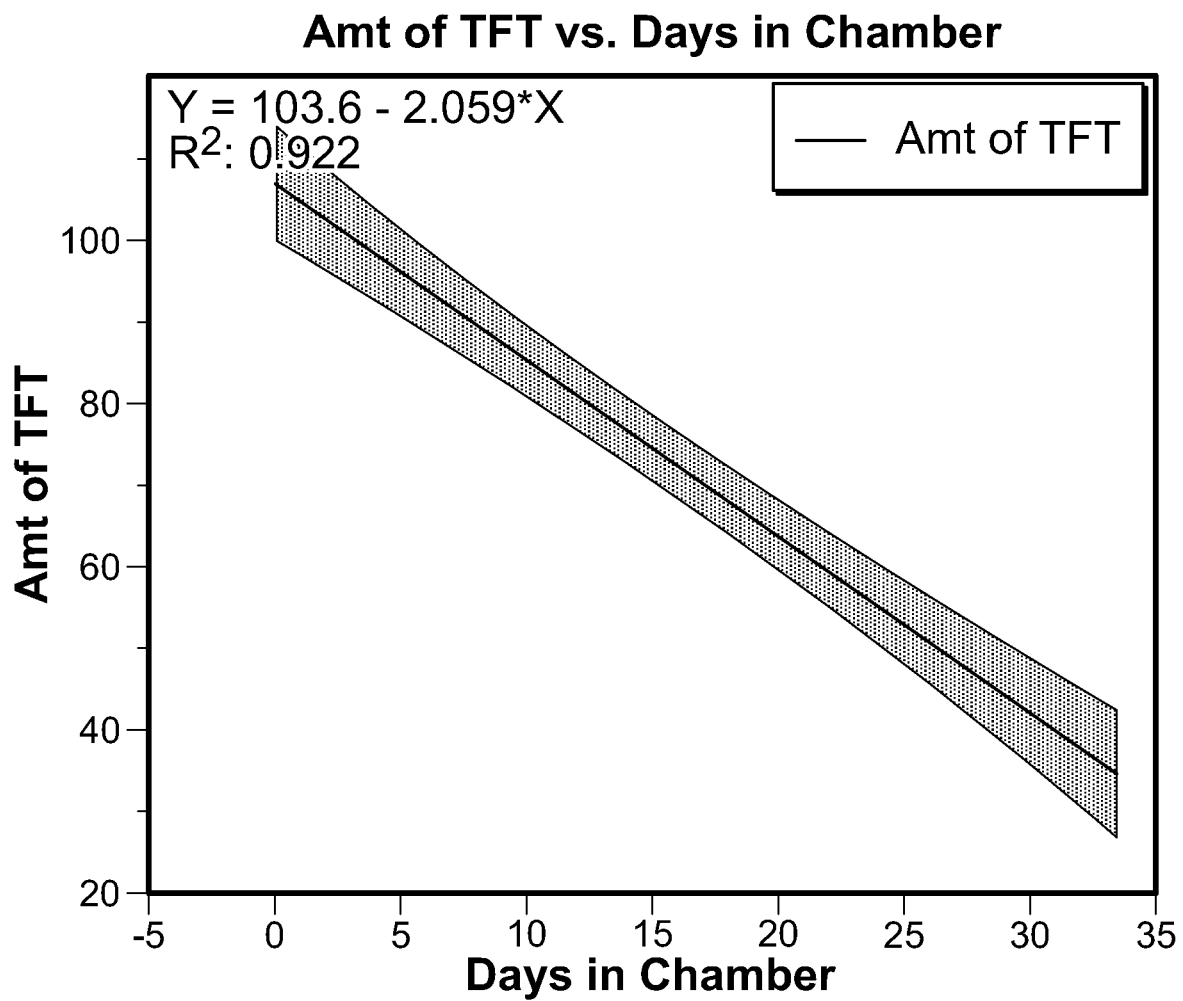
FIG. 24 is a graph illustrating the emanation rate of a volatile material from the dispensing device of FIG. 22 at a loading level of 110 mg of an active agent.

The dispensing devices were also subsequently tested based on their effectiveness of emanating the volatile material or active agent therein. In particular, dispensing devices incorporating a high-density polyethylene as the outer layer 46, 132, a nylon-based material as the inner layer 50, 136, and an ethylene vinyl acetate as the sealant layer 52, 138 were constructed. The dispensing devices were then dosed with approximately 137.5 mg of volatile material, including 110 mg of transfluthrin as an active agent, and hermetically heat sealed. Next, the dispensing devices were opened to expose an interior thereof and allowed to emanate within a closed chamber for approximately 32 days. The amount of transfluthrin still contained within the dispensing devices was measured at multiple instances, including after 5 days from initial exposure, after 13 days from initial exposure, after 20 days from initial exposure, and after 32 days from initial exposure. The data from this experiment was subsequently graphed and is visually shown in FIG. 24. As shown in FIG. 24, the dispensing devices provide a controlled release of the active agent (i.e., transfluthrin) from the dispensing device for a period in excess of 30 days.

Example 5

Figure 25:
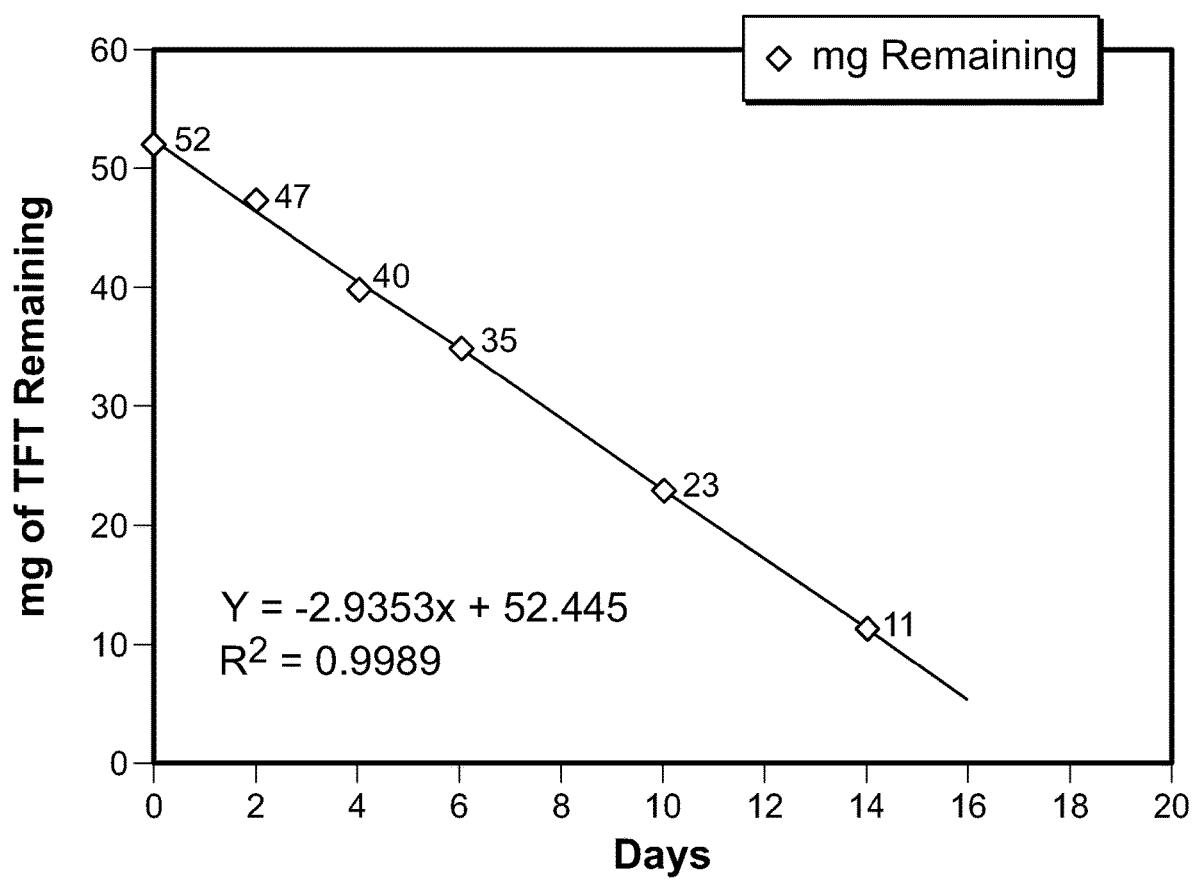
FIG. 25 is a graph illustrating the emanation rate of a volatile material from a dispensing device having a low loading level of 55 mg of an active agent.

Other dispensing devices similar to the dispensing devices previously discussed in Example 4 were subsequently tested based on their effectiveness of emanating a volatile material or active agent therein at an initial dosage level of 55 mg. In particular, dispensing devices similar to the dispensing devices discussed in Example 5 were dosed with approximately 55 mg of transfluthrin as an active agent, and allowed to emanate within a closed chamber for approximately 14 days. The amount of transfluthrin still contained within the dispensing devices was measured at multiple instances, including after 2 days from initial exposure, after 4 days from initial exposure, after 6 days from initial exposure, after 10 days from initial exposure, and after 14 days from initial exposure. The data from this experiment was subsequently graphed and is visually shown in FIG. 25. As shown in FIG. 25, the dispensing devices provide a controlled release of the active agent (i.e., transfluthrin) from the dispensing device for a period in excess of 14 days.

As previously discussed, although amounts of an initial dosage are outlined herein with regard to particular embodiments, it should be understood by one skilled in the art that the initial dosage may vary and may be dependent on a combination of factors, including but not limited to, the surface area of the interior 62 of the dispensing device 10, 110 to which the volatile material is applied, the thickness of the one or more layers to which the volatile material may be applied (e.g., a thickness of the inner layer 50, 136 or a thickness of a sealant layer 52, 138, individually or in combination), a desired delivery rate of the volatile material from the dispensing device 10, 110, a type of material(s) used for the one or more layers of the dispensing device 10, 110 (e.g., a type of material(s) used for the inner layer 50, 110, a type of material(s) used for the sealant layer 52, 138, a type of material(s) used for the outer layer 46, 112, or a type of material(s) used for the sealant layer 48, 134), or a type of volatile material(s) used in the dispensing device 10, 110. For example, in one embodiment, a dispensing device 10, 110 may have an initial dosage of 110 mg of active agent if emanation is desired for longer than 30 days, as shown in FIG. 24. Alternatively, as shown in FIG. 25, a dispensing device 10, 110 may have an initial dosage of 55 mg of active agent if emanation is desired for a shorter period of time, such as 14 days or two weeks.

The term "about," as used herein, refers to variation in the numerical quantity that may occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" may also encompass amounts that differ due to different equilibrium conditions for a composition resulting from a particular initial mixture. In one embodiment, the term "about" refers to a range of values±5% of a specified value.

The term "weight percent," "wt. %," "percent by weight," "% by weight," and variations thereof, as used herein, refer to the concentration of a substance, material, component, or chemical as the weight of that substance, material, component, or chemical divided by the total weight, for example, of the composition or of a particular component of the composition, and multiplied by 100. It is understood that, as used herein, "percent," "%," and the like may be synonymous with "weight percent," "w %." For example, in connection with the volatile material discussed herein and the wt. % values thereof, the wt. % of the active agent discussed herein may be with regard to the weight of the active agent divided by the total weight of the volatile material, which may include the weight of the active agent and the weight of a solvent.

Variations and modifications of the foregoing are within the scope of the present disclosure. It is understood that the embodiments disclosed and defined herein extend to all alternative combinations of two or more of the individual features mentioned or evident from the text and/or drawings. All of these different combinations constitute various alternative aspects of the present disclosure. The embodiments described herein explain the best modes known for practicing the disclosure and will enable others skilled in the art to utilize the disclosure. The claims are to be construed to include alternative embodiments to the extent permitted by the prior art.

As noted previously, it will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

INDUSTRIAL APPLICABILITY

The aspects of the dispenser or dispensing device described herein advantageously combine the features of a layer, or combination of layers, that effectively retain or store a volatile material or active agent, effectively seal a volatile material or active agent within the dispenser or dispensing device, and effectively emanate the volatile material or active agent at a desired time of use. Additionally, the aspects of the dispenser or dispensing device provides a mechanism that is both easy to use and inexpensive, as well as a device that is structurally stable. Accordingly, the disclosed dispenser or dispensing device may be used across a broad range of applications.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A multi-layer article including a non-active state and an active state, the multi-layer article comprising:
   an outer layer formed from a high crystalline polymer structure, and having a first side and a second side;
   an inner layer adjacent to at least a portion of the outer layer and including a material selected from the group consisting of a polyethylene, a polyvinyl alcohol, a polypropylene, an ethylene-vinyl acetate, a high-density polyethylene, and an ethylene vinyl alcohol, the inner layer being bonded to the outer layer in both the active state and the non-active state, wherein the inner layer includes a volatile material therein; and
   an upper layer adjacent to at least a portion of the inner layer and including a material selected from the group consisting of an ethylene-vinyl acetate, a polyethylene, a polypropylene, an ethylene vinyl alcohol copolymer, a polyester, a nylon or polybutene, butylene copolymer, and/or combinations of these materials,
   wherein the upper layer includes a first side and a second side opposite the first side, the first side of the upper layer being disposed atop at least a portion of the inner layer and the volatile material included therein,
   wherein the multi-layer article is folded upon itself in the non-active state so that at least a first portion of the second side of the upper layer is disposed on a second portion of the second side of the upper layer, and
   wherein the first portion and the second portion of the upper layer are heat-sealed in the non-active state.

2. The multi-layer article of claim 1, wherein the outer layer is a high-density polyethylene film, the inner layer is a nylon-based film, and the upper layer is a blend of ethylene vinyl acetate with polyolefin film.

3. The multi-layer article of claim 2, wherein the volatile material comprises an active agent and a solvent.

4. The multi-layer article of claim 3, wherein the active agent is transfluthrin and the solvent is a di-propylene gl 5. The multi-layer article of claim 4, wherein the multi-layer article is initially dosed with about 110 mg of the active agent.

6. The multi-layer article of claim 5, wherein when the multi-layer article is in the non-active state, the multi-layer article retains at least 90% of the initial dosage of the active agent after 30 days.

7. The multi-layer article of claim 6, wherein when the multi-layer article is in the active state, the multi-layer article emanates the active agent at an emanation rate between about 2 mg/day and about 4 mg/day.

8. The multi-layer article of claim 7, wherein the multi-layer article has a peel strength between about 2 N and about 50 N, the peel strength being an average load strength capable of separating a heat seal between the first and second portion of the upper layer.

9. A multi-layer article including a non-active state and an active state, the multi-layer article comprising:
- an outer layer having a first side and a second side;
- an inner layer adjacent to at least a portion of the outer layer and including a volatile material therein in both the active state and the non-active state, the inner layer being bonded to the outer layer in both the active state and the non-active state; and
- an upper layer including a first side and a second side, the first side of the upper layer being positioned on an upper surface of at least a portion of the inner layer and the volatile material included therein,
- wherein the volatile material includes a solvent and an active agent,
- wherein the multi-layer article is folded upon itself in the non-active state so that at least a first portion of the second side of the upper layer is disposed on a top of a second portion of the second side of the upper layer, and
- wherein the first portion and the second portion of the upper layer are heat-sealed in the non-active state.

10. A multi-layer article including a non-active state and an active state, the multi-layer article comprising:
- an outer layer having a first side and a second side;
- an inner layer adjacent to at least a portion of the outer layer and including a volatile material therein, the inner layer being bonded to the outer layer in both the active state and the non-active state; and
- an upper layer including a first side and a second side, the first side of the upper layer being disposed on top of at least a portion of the inner layer and the volatile material therein;
- wherein the volatile material includes an active agent,
- wherein the multi-layer article is folded upon itself in the non-active state so that at least a first portion of the second side of the upper layer is disposed on a top of a second portion of the second side of the upper layer, and
- wherein the first portion and the second portion of the upper layer are heat-sealed in the non-active state.

11. The multi-layer article of claim 9, wherein the outer layer includes a high-density polyethylene.

12. The multi-layer article of claim 11, wherein the inner layer includes a nylon.

13. The multi-layer article of claim 12, wherein the upper layer is an ethylene vinyl acetate with polyolefin.

14. The multi-layer article of claim 13, wherein the volatile material comprises the active agent and a solvent.

15. The multi-layer article of claim 14, wherein the active agent is transfluthrin and the solvent is a di-propylene glycol dimethyl ether.

16. The multi-layer article of claim 14, wherein the multi-layer article is initially dosed with about 110 mg of the active agent.

17. The multi-layer article of claim 16, wherein when the multi-layer article is in the non-active state, the multi-layer article retains at least 90% of the initial dosage of the active agent after 60 days.

18. The multi-layer article of claim 17, wherein when the multi-layer article is in the active state, the multi-layer article emanates the active agent at an emanation rate between about 2 mg/day and about 4 mg/day.

19. The multi-layer article of claim 9, wherein the multi-layer article has a peel strength between about 2 N and about 50 N, the peel strength being an average load strength capable of separating a heat seal between the first and second portion of the upper layer.

20. The multi-layer article of claim 14, wherein the active agent and the inner layer have a relative energy difference between 0.5 and 15.

21. The multi-layer article of claim 9, the inner layer having a first side and a second side, wherein the volatile material is included between the first side and the second side of the inner layer.

* * * * *